US006818748B2

(12) United States Patent
Fulton et al.

(10) Patent No.: US 6,818,748 B2
(45) Date of Patent: Nov. 16, 2004

(54) CLONING, EXPRESSION, SEQUENCING, AND FUNCTIONAL ENHANCEMENT OF MONOCLONAL SCFV ANTIBODY AGAINST VENEZUELAN EQUINE ENCEPHALITIS VIRUS (VEE)

(75) Inventors: R. Elaine Fulton, Medicine Hat (CA); Leslie Nagata, Medicine Hat (CA); Azhar Alvi, Mississauga (CA)

(73) Assignee: Her Majesty the Queen in right of Canada, as represented by the Minister of National Defence, Ottawa (CA)

( * ) Notice: Subject to any disclaimer, the term of this patent is extended or adjusted under 35 U.S.C. 154(b) by 0 days.

(21) Appl. No.: 10/096,246

(22) Filed: Mar. 13, 2002

(65) Prior Publication Data

US 2003/0100060 A1 May 29, 2003

Related U.S. Application Data

(60) Provisional application No. 60/275,103, filed on Mar. 12, 2001, and provisional application No. 60/341,843, filed on Dec. 21, 2001.

(51) Int. Cl.[7] .......................... C12P 21/08; C07K 1/00; C07H 21/02
(52) U.S. Cl. ................ 530/387.3; 530/389.4; 530/866; 536/23.1
(58) Field of Search .................... 530/387.3, 389.4, 530/866; 536/23.1, 23.53; 435/69.1

(56) References Cited

PUBLICATIONS

Roehrig et al., "The Neutralization Site on the E2 Glycoprotein of Venezuelan Equine Encephalomyelitis (TC–83) Virus is Composed of Multiple Conformationally Stable Epitopes," Virology, vol. 142, pp. 347–356, Academic Press, Inc. (1985).

Alvi et al., "Development of a Functional Monoclonal Single–Chain Variable Fragment Antibody Against Venezuelan Equine Encephalitis Virus," Hybridoma, vol. 18, No. 5, Mary Ann Leibert, Inc. (1999).

Shibata et al., "Construction of a Functional Single–Chain Variable Fragment Antibody Against Hemagglutinin From *Porphyromonas gingvalis*," Infection and Immunity, vol. 66, No. 5, pp. 2207–2212, American Society for Microbiology (May 1998).

Roehrig et al., "Use of a New Synthetic–Peptide–Derived Monoclonal Antibody to Differentiate between Vaccine and Wild–Type Venezuelan Equine Encephalomyelitis Viruses," Journal of Clinical Microbiology, vol. 29, No. 3, pp. 630–631, American Society for Microbiology (Mar. 1991).

Roehrig et al., "Antigenic Analysis of the Surface Glycoproteins of a Venezuelan Equine Encephalomyelitis Virus (TC–83) Using Monoclonal Antibodies," Virology, No. 118, pp. 269–278, Academic Press, Inc. (1982).

*Primary Examiner*—Hankyel T. Park
(74) *Attorney, Agent, or Firm*—Rader, Fishman & Grauer PLLC

(57) ABSTRACT

A single chain variable fragment (ScFv) antibody from a monoclonal antibody (Mab) against Venezuelan equine encephalitis (VEE) virus, is generated by cloning linked variable regions of the heavy ($V_H$) and the light ($V_L$) chain antibody genes. Mab clone $1A_4A_1$ in *E. coli* strain TG-1 was successfully cloned as ScFv. Results were reproduced in *E. coli* strain HB2151, expressing the same clone, A116, though displaying weak binding specificity to VEE due to a frame shift in the N-terminal region of the $V_L$ domain, upstream to the complementarity-determining region 1. A PCR-based site-directed mutagenesis approach was adopted to re-introduce the three single-base deletions in the 5 prime region of the $V_L$ gene of A116, corresponding to framework-1 region, producing mutant MA116, correcting a localized frame-shift in framework-1 region to consensus framework-1 amino acid sequence. A MA116 clone, MA116-15, shows comparable reactivity to the parental Mab in recognizing VEE antigen.

27 Claims, 19 Drawing Sheets

A. Cloning and PCR

B. Expression and analysis

Figure 5A

```
Start V_H                              CDR-H1
MAQVQLQESGPELVKPGASVKISCKAS GYTFTDYHVH WVK    A116
MAQVQLQQSGAELVRPGASVTLSCKAS DYTFTDYEMH WVK    D66
HSQVQLQQPGAELVKPGASVKLSCKAS GYTFTSYWMH WVK    MHMS18
DGQVQLQQPGAELVKPGASVKLSCKAS GYTFTSYWMH WVK    PC4402
E--VQLQQSGAELVKPGASVKLSCKAS GYTFTSYWMH WVK    S41394

CDR-H2
GKPGQGLEWIG MTYPGFDNTNYSETFKG KATLTVDTFSTT    A116
QTPVHGLKWIG AIDPETGGTAYNQKFKG RATLTADKSSTT    D66
QRPGRGLEWIG RIDPNSGGTKYNEKFKS KATLTVDKPSST    MHMS18
QRPGRGLEWIG RIDPNSGGTKYNEKFKS KATLTVDKPSST    PC4402
QRPGQGLEWIG EIDPSDSYTYYNQKFKG KATLTVDKSSST    S41394

CDR-H3
VYMQLSSLTSEDTVVYFCAR G--VG----LDY WGQGTTVT    A116
AYMELRSLTSEDSAVYYCTR Y--YGNPW-PAY WGQGTTVT    D66
AYMQLSSLTSEDSAVYYCAR YDYYGSSY-FDY WGQGTTLT    MHMS18
AYMQLSSLTSEDSAVYYCAR YDYYGSSY-FDY WGQGTTLT    PC4402
AYMQFSSLTSEDSAVYYCAR -RYYGSRVSMDY WGQGTSVT    S41394

VSS    A116
VSS    D66
VSS    MHMS18
VSS    PC4402
VSS    S41394
```

V_H amino acid comparisons

Figure 5B

```
Start V_L                                    CDR-L1
DSSSLVS-KFVSTSIGDRIRITC KASQDVDTAVG WYQQRP    A116
DIELTQSPASLSVSVGETVTITC RASENIYRNLA WYQQKQ    D66
DIQMTQSPASLSASVGETVTITC RASENIYSYLA WYQQKQ    B47329
DIQMTQSPASLSASVGETVTIIC RASVNIYSYLA WYQQKQ    S11245
DIQMTQSPASLSASVGETVTITC RASGNIHNYLA WYQQKP    S19112
-------PASLSASVGETCTITC RASENIYSYLA WYQQKQ    S20810
DIQMTQSPASLSASVGETVTITC RASENTYSYLA WYQQKQ    S31488

CDR-L2
GQSPKLLIF WSSTRHT GVPDRFTGSGSGTDFTLTISNVQS    A116
GKSPQLLVY AATNLAD GVPSRFSGSGSGTQYSLKINSLKS    D66
GKSPQLLVY NAKTLAE GVPSRFSGSGSGTQFSLKINSLQP    B47329
GKSPQLLVY NAKILAE GVPSRFSGSGSGTQFSLKINSLQP    S11245
GKSPQLLVY NAKTLAD GVPSRFSGSGSGTQYSLKINSLQP    S19112
GKSPQLLVY NAKTLAE GVPSRFSGSGSGTQFSLKINSLQP    S20810
GKSPQLLVY NAKTLAE GVPSRFSGSGSGTQFSLKINSLQP    S31488

CDR-L3
EDLADYFC HQYSSHPFT FGSGTKLEIKRAAA             A116
EDFGSYYC QHFWGTPYT FGGGTKLEIKRA-A             D66
EDFGSYYC QHHYGTPFT FGSGTKLEI                  B47329
EDFGSYYC QHHYG-PFT FGSGTKLEIKRADA             S11245
EDFGSYYC QHFWSTPWT FGGGTKLEIKR                S19112
EDFGRYYC QHVYGTPYT FGGGTKLEIKR                S20810
EDFGSYYC QHHYGTPFT FGSGTKLEIKR                S31488
```

V_L amino acid comparisons

Figure 6

```
ACATCGAGCTCACTCAGTCTCCAAATTCGT-GTCCACATC   1A4A1-10
ACATCGAGCTCACTCAATCTCCATCCTCCTTATCTGCCTC   1A4A1-12
ACATCGAGCTCACTCAGTCTCCATCCTCCTTATCTGCCTC   1A4A1-17
ACATCGAGCTCACTCAGTCTCCAAATTCGT-GTCCACATC   1A4A1-24
ACATCGAGCTCACTCAGTCTCCAAATTCGT-GTCCACATC   1A4A1-30
AC-TCGAGCTCACTC-GTCTCCAAATTCGT-GTCCACATC   1A4A1-16
   A            A             T
```

Figure 11

```
397                                              436
GAC-TCGAGC TCACTC-GTC CTC-CAAATTC GT-GTCCACA        A116-6
GAC-TCGAGC TCACTC-GTC CTC-CAAATTC GT-GTCCACA        MA116-6
G-CATCGAGC TCACTCAGTC CTCTCAAATTC GTTGTCCACA        MA116-4
GACATCGAGC TCACTCAGTC CTCCCAAATTC GTTGTC-ACA        MA116-14
GACATCGAGC TCACTCAGTC CTC-CAAATTC GTTGTCCACA        MA116-16
GACATCGAGC TCACTCAGTC CTC-CAAATTC GTTGTCCACA        MA116-15
```

Figure 12

|  | 10 | 20 | 30 | 40 | |
|---|---|---|---|---|---|
| 1 | M A Q V Q L Q E S G P E L V K P G A S V K I S C K A S G Y T F T D Y H V H W V K | A116-6 |
| 1 | M A Q V Q L Q E S G P E L V K P G A S V K I S C K A S G Y T F T D Y H V H W V K | MA116-6 |
| 1 | M A Q V Q L Q E S G P E L V K P G A S V K I S C K A S G Y T F T D Y H V H W V K | MA116-4 |
| 1 | M A Q V Q L Q E S G P E L V K P G A S V K I S C K A S G Y T F T D Y H V H W V K | MA116-14 |
| 1 | M A Q V Q L Q E S G P E L V K S G A S V K I S C K A S G Y T F T D Y H V H W V K | MA116-16 |
| 1 | M A Q V Q L Q E S G P E L V K P G A S V K I S C K A S G Y T F T D Y H V H W V K | MA116-15 |

|  | 50 | 60 | 70 | 80 | |
|---|---|---|---|---|---|
| 41 | G K P G Q G L E W I G M T Y P G F D N T N Y S E T F K G K A T L T V D T F S T T | A116-6 |
| 41 | G K P G Q G L E W I G M T Y P G F D D T N Y S E T F K G K A T L T V D T S S N T | MA116-6 |
| 41 | G K P G Q G L E W I G M T Y P G F D N T N Y S E T F K G K A T L T V D T S S N T | MA116-4 |
| 41 | G K P G Q G L E W I G M T Y P G F D N T N Y S E T F K G K A T L T V D T S S N T | MA116-14 |
| 41 | G K P G Q G L E W I G M T Y P G F D N T N Y S E T F K G K A T L T V D T S S N T | MA116-16 |
| 41 | G K P G Q G L E W I G M T Y P G F D N T N Y S E T F K G K A T L T V D T S S N T | MA116-15 |

|  | 90 | 100 | 110 | 120 | |
|---|---|---|---|---|---|
| 81 | V Y M Q L S S L T S E D T V V Y F C A R G V G L D Y W G Q G T T V T V S S G G G | A116-6 |
| 81 | V Y M Q L S S L T S E D T A V Y F C A R G V G L D Y W G Q G T T V T V S S G G G | MA116-6 |
| 81 | V Y M Q L S S L T S E D T A V Y F C A R G V G L D Y W G Q G T T V T V S S G G G | MA116-4 |
| 81 | V Y M Q L S S L T S E D T A V Y F C A R G V G L D Y W G Q G T T V T V S S G G G | MA116-14 |
| 81 | V Y M Q L S S L T S E D T A V Y F C A R G V G L D Y W G Q G T T V T V S S G G G | MA116-16 |
| 81 | V Y M Q L S S L T S E D T A V Y F C A R G V G L D Y W G Q G T T V T V S S G G G | MA116-15 |

|  | 130 | 140 | 150 | 160 | |
|---|---|---|---|---|---|
| 121 | G S G G G S G G G G S D S S L - V S K F V S T S I G D R I R I T C K A S Q D | A116-6 |
| 121 | G S G G G S G G G G S D S S L - V S K F V S T S I G D R I R I T C K A S Q D | MA116-6 |
| 121 | G S G G G S G G G G S A S S L S L S N S L S T S I G D R I R I T C K A S Q D | MA116-4 |
| 121 | G S G G G S G G G G S D I E L T Q S P K F V V T S I G D R I R I T C K A S Q D | MA116-14 |
| 121 | G S G G G S G G G G S D I E L T Q S P N S L S T S I G D R I R I T C K A S Q D | MA116-16 |
| 121 | G S G G G S G G G G S D I E L T Q S P N S L S T S I G D R I R I T C K A S Q D | MA116-15 |

|  | 170 | 180 | 190 | 200 | |
|---|---|---|---|---|---|
| 160 | V D T A V G W Y Q Q R P G Q S P K L L I F W S S T R H T G V P D R F T G S G S G | A116-6 |
| 160 | V D T A V G W Y Q Q R P G Q S P K L L I F W S S T R H T G V P D R F T G S G S G | MA116-6 |
| 161 | V D T A V G W Y Q Q R P G Q S P K L L I F W S S T R H T G V P D R F T G S G S G | MA116-4 |
| 161 | V D T A V G W Y Q Q R P G Q S P K L L I F W S S T R H T G V P D R F T G S G S G | MA116-14 |
| 161 | V D T A V G W Y Q Q R P G Q S P K L L I F W S S T R H T G V P D R F T G S G S G | MA116-16 |
| 161 | V D T A V G W Y Q Q R P G Q S P K L L I F W S S T R H T G V P D R F T G S G S G | MA116-15 |

|  | 210 | 220 | 230 | 240 | |
|---|---|---|---|---|---|
| 200 | T D F T L T I S N V Q S E D L A D Y F C H Q Y S S H P F T F G S G T K L E I K R | A116-6 |
| 200 | T D F T L T I S N V Q S E D L A D Y F C H Q Y S S Y P F T F G S G T K L E I K R | MA116-6 |
| 201 | T D F T L T I S N V Q S E D L A D Y F C H Q Y S S Y P F T F G S G T K L E I K R | MA116-4 |
| 201 | T D F T L T I S N A Q S E D L A D Y F C H Q Y S S Y P F T F G S G T K L E I K R | MA116-14 |
| 201 | T D F T L T I S N V Q S E D L A D Y F C H Q Y S S Y P F T F G S G T K L E I K R | MA116-16 |
| 201 | T D F T L T I S N V Q S E D L A D Y F C H Q Y S S Y P F T F G S G T K L E I K R | MA116-15 |

Figure 13A
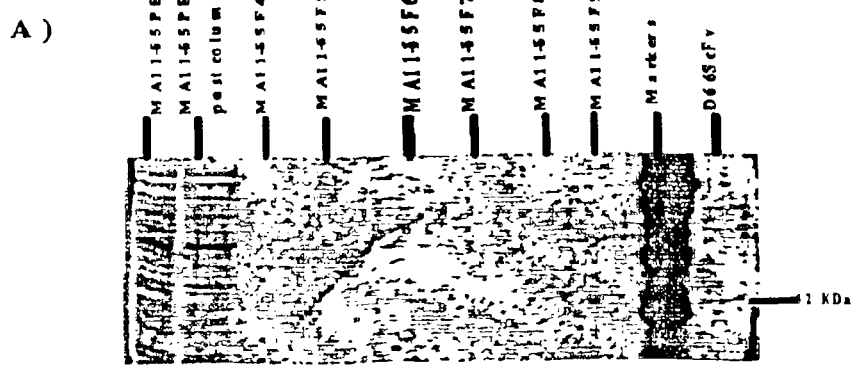
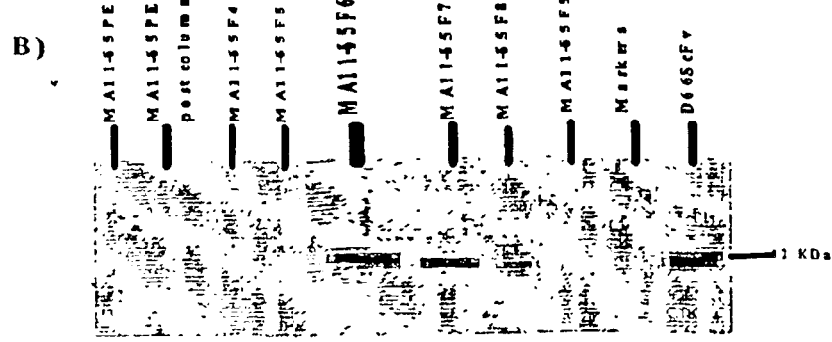
Figure 13B

SEQUENCE LISTING

<160> NUMBER OF SEQ ID NOS: 39

<210> SEQ ID NO 1
<211> LENGTH: 774
<212> TYPE: DNA
<213> ORGANISM: mouse
<220> FEATURE:
<221> NAME/KEY: CDS
<222> LOCATION: (1)..(774)
<223> OTHER INFORMATION: scFv protein A116-6    1 - 717
      e-tag       718 - 774

<400> SEQUENCE: 1

```
atg gcc cag gtc caa ctg cag gag tca gga cct gag ctg gtg aag cct      48
Met Ala Gln Val Gln Leu Gln Glu Ser Gly Pro Glu Leu Val Lys Pro
1               5                   10                  15 ggg gct tca gtg aag ata tcc tgc aag gcc tct ggc tac acc ttc act      96
Gly Ala Ser Val Lys Ile Ser Cys Lys Ala Ser Gly Tyr Thr Phe Thr
            20                  25                  30 gac tac cat gtt cac tgg gtg aag ggg aag cct gga cag gga ctt gaa     144
Asp Tyr His Val His Trp Val Lys Gly Lys Pro Gly Gln Gly Leu Glu
        35                  40                  45 tgg att gga atg act tat cct gga ttc gat aat act aat tac agt gag     192
Trp Ile Gly Met Thr Tyr Pro Gly Phe Asp Asn Thr Asn Tyr Ser Glu
    50                  55                  60 act ttc aag ggc aag gcc aca ttg act gta gac aca ttc tcc acc aca     240
Thr Phe Lys Gly Lys Ala Thr Leu Thr Val Asp Thr Phe Ser Thr Thr
65                  70                  75                  80 gtc tac atg cag ctc agc agc ctg aca tct gag gac acc gtt gtc tat     288
Val Tyr Met Gln Leu Ser Ser Leu Thr Ser Glu Asp Thr Val Val Tyr
                85                  90                  95 ttt tgt gca aga ggt gtg ggc ctt gac tac tgg ggc caa ggg acc acg     336
Phe Cys Ala Arg Gly Val Gly Leu Asp Tyr Trp Gly Gln Gly Thr Thr
            100                 105                 110 gtc acc gtc tcc tca ggt gga ggc ggt tca ggc gga ggt ggc tct ggc     384
Val Thr Val Ser Ser Gly Gly Gly Gly Ser Gly Gly Gly Gly Ser Gly
        115                 120                 125 ggt ggc gga tcg gac tcg agc tca ctc gtc tcc aaa ttc gtg tcc aca     432
```

-continued

| | | |
|---|---|---|
| Gly Gly Gly Ser Asp Ser Ser Ser Leu Val Ser Lys Phe Val Ser Thr<br>130 135 140 | | |
| tca ata gga gac agg atc aga atc acc tgc aag gcc agt cag gat gtg<br>Ser Ile Gly Asp Arg Ile Arg Ile Thr Cys Lys Ala Ser Gln Asp Val<br>145 150 155 160 | 480 | |
| gat act gct gta ggc tgg tat caa cag aga cca ggg caa tct cct aaa<br>Asp Thr Ala Val Gly Trp Tyr Gln Gln Arg Pro Gly Gln Ser Pro Lys<br>165 170 175 | 528 | |
| cta ctg att ttc tgg tca tcc acc cgg cac act gga gtc cct gat cgc<br>Leu Leu Ile Phe Trp Ser Ser Thr Arg His Thr Gly Val Pro Asp Arg<br>180 185 190 | 576 | |
| ttc aca ggc agt gga tct ggg aca gat ttc act ctc acc att agc aat<br>Phe Thr Gly Ser Gly Ser Gly Thr Asp Phe Thr Leu Thr Ile Ser Asn<br>195 200 205 | 624 | |
| gtg cag tct gaa gac ttg gca gat tat ttc tgt cac caa tat agc agc<br>Val Gln Ser Glu Asp Leu Ala Asp Tyr Phe Cys His Gln Tyr Ser Ser<br>210 215 220 | 672 | |
| cat cca ttc acg ttc ggc tcg ggg aca aag ttg gaa ata aaa cgg gcg<br>His Pro Phe Thr Phe Gly Ser Gly Thr Lys Leu Glu Ile Lys Arg Ala<br>225 230 235 240 | 720 | |
| gcc gca ggt gcg ccg gtg ccg tat ccg gat ccg ctg gaa ccg cgt gcc<br>Ala Ala Gly Ala Pro Val Pro Tyr Pro Asp Pro Leu Glu Pro Arg Ala<br>245 250 255 | 768 | |
| gca tag<br>Ala | 774 | |

<210> SEQ ID NO 2
<211> LENGTH: 257
<212> TYPE: PRT
<213> ORGANISM: mouse
<220> FEATURE:
<221> NAME/KEY: MISC_FEATURE
<223> OTHER INFORMATION: scFv protein A116-6  1 - 239
       e-tag                               240 - 257

<400> SEQUENCE: 2

Met Ala Gln Val Gln Leu Gln Glu Ser Gly Pro Glu Leu Val Lys Pro
1               5                   10                  15

Gly Ala Ser Val Lys Ile Ser Cys Lys Ala Ser Gly Tyr Thr Phe Thr
            20                  25                  30

Asp Tyr His Val His Trp Val Lys Gly Lys Pro Gly Gln Gly Leu Glu
        35                  40                  45

Trp Ile Gly Met Thr Tyr Pro Gly Phe Asp Asn Thr Asn Tyr Ser Glu
    50                  55                  60

Thr Phe Lys Gly Lys Ala Thr Leu Thr Val Asp Thr Phe Ser Thr Thr
65                  70                  75                  80

Val Tyr Met Gln Leu Ser Ser Leu Thr Ser Glu Asp Thr Val Tyr
                85                  90                  95

Phe Cys Ala Arg Gly Val Gly Leu Asp Tyr Trp Gly Gln Gly Thr Thr
            100                 105                 110

Val Thr Val Ser Ser Gly Gly Gly Ser Gly Gly Gly Ser Gly
        115                 120                 125

Gly Gly Gly Ser Asp Ser Ser Ser Leu Val Ser Lys Phe Val Ser Thr
    130                 135                 140

Ser Ile Gly Asp Arg Ile Arg Ile Thr Cys Lys Ala Ser Gln Asp Val
145                 150                 155                 160

Asp Thr Ala Val Gly Trp Tyr Gln Gln Arg Pro Gly Gln Ser Pro Lys
                165                 170                 175

```
Leu Leu Ile Phe Trp Ser Ser Thr Arg His Thr Gly Val Pro Asp Arg
            180                 185                 190

Phe Thr Gly Ser Gly Ser Gly Thr Asp Phe Thr Leu Thr Ile Ser Asn
        195                 200                 205

Val Gln Ser Glu Asp Leu Ala Asp Tyr Phe Cys His Gln Tyr Ser Ser
    210                 215                 220

His Pro Phe Thr Phe Gly Ser Gly Thr Lys Leu Glu Ile Lys Arg Ala
225                 230                 235                 240

Ala Ala Gly Ala Pro Val Pro Tyr Pro Asp Pro Leu Glu Pro Arg Ala
                245                 250                 255

Ala
```

<210> SEQ ID NO 3
<211> LENGTH: 774
<212> TYPE: DNA
<213> ORGANISM: mouse
<220> FEATURE:
<221> NAME/KEY: CDS
<222> LOCATION: (1)..(774)
<223> OTHER INFORMATION: scFv protein MA116-6  1 - 717
      etag          718 - 774

<400> SEQUENCE: 3

```
atg gcc cag gtc caa ctg cag gag tca gga cct gag ctg gtg aag cct      48
Met Ala Gln Val Gln Leu Gln Glu Ser Gly Pro Glu Leu Val Lys Pro
1               5                   10                  15 ggg gct tca gtg aag ata tcc tgc aag gcc tct ggc tac acc ttc act      96
Gly Ala Ser Val Lys Ile Ser Cys Lys Ala Ser Gly Tyr Thr Phe Thr
            20                  25                  30 gac tac cat gtt cac tgg gtg aag ggg aag cct gga cag gga ctt gaa     144
Asp Tyr His Val His Trp Val Lys Gly Lys Pro Gly Gln Gly Leu Glu
        35                  40                  45 tgg att gga atg act tat cct gga ttc gat gat act aat tac agt gag     192
Trp Ile Gly Met Thr Tyr Pro Gly Phe Asp Asp Thr Asn Tyr Ser Glu
    50                  55                  60 act ttc aag ggc aag gcc aca ttg act gta gac aca tcc tcc aac aca     240
Thr Phe Lys Gly Lys Ala Thr Leu Thr Val Asp Thr Ser Ser Asn Thr
65                  70                  75                  80 gtc tac atg cag ctc agc agc ctg aca tct gag gac act gct gtc tat     288
Val Tyr Met Gln Leu Ser Ser Leu Thr Ser Glu Asp Thr Ala Val Tyr
                85                  90                  95 ttt tgt gca aga ggt gtg ggc ctt gac tac tgg ggc caa ggg acc acg     336
Phe Cys Ala Arg Gly Val Gly Leu Asp Tyr Trp Gly Gln Gly Thr Thr
            100                 105                 110 gtc acc gtc tcc tca ggt gga ggc ggt tca ggc gga ggt ggc tct ggc     384
Val Thr Val Ser Ser Gly Gly Gly Gly Ser Gly Gly Gly Gly Ser Gly
        115                 120                 125 ggt ggc gga tcg gac tcg agc tca ctc gtc tcc aaa ttc gtg tcc aca     432
Gly Gly Gly Ser Asp Ser Ser Ser Leu Val Ser Lys Phe Val Ser Thr
    130                 135                 140 tca ata gga gac agg atc aga atc acc tgc aag gcc agt cag gat gtg     480
Ser Ile Gly Asp Arg Ile Arg Ile Thr Cys Lys Ala Ser Gln Asp Val
145                 150                 155                 160 gat act gct gta ggc tgg tat caa cag aga cca ggg caa tct cct aaa     528
Asp Thr Ala Val Gly Trp Tyr Gln Gln Arg Pro Gly Gln Ser Pro Lys
                165                 170                 175 cta ctg att ttc tgg tca tcc acc cgg cac act gga gtc cct gat cgc     576
Leu Leu Ile Phe Trp Ser Ser Thr Arg His Thr Gly Val Pro Asp Arg
            180                 185                 190 ttc aca ggc agt gga tct ggg aca gat ttc act ctc acc att agc aat     624
Phe Thr Gly Ser Gly Ser Gly Thr Asp Phe Thr Leu Thr Ile Ser Asn
```

-continued

```
Phe Thr Gly Ser Gly Ser Gly Thr Asp Phe Thr Leu Thr Ile Ser Asn
        195                 200                 205 gtg cag tct gaa gac ttg gca gat tat ttc tgt cac caa tat agc agc        672
Val Gln Ser Glu Asp Leu Ala Asp Tyr Phe Cys His Gln Tyr Ser Ser
        210                 215                 220 tat cca ttc acg ttc ggc tcg gga aca aag ttg gaa ata aaa cgg gcg        720
Tyr Pro Phe Thr Phe Gly Ser Gly Thr Lys Leu Glu Ile Lys Arg Ala
225                 230                 235                 240 gcc gca ggt gcg ccg gtg ccg tat ccg gat ccg ctg gaa ccg cgt gcc        768
Ala Ala Gly Ala Pro Val Pro Tyr Pro Asp Pro Leu Glu Pro Arg Ala
                245                 250                 255 gca tag                                                                 774
Ala

<210> SEQ ID NO 4
<211> LENGTH: 777
<212> TYPE: DNA
<213> ORGANISM: mouse
<220> FEATURE:
<221> NAME/KEY: CDS
<222> LOCATION: (1)..(777)
<223> OTHER INFORMATION: scFv protein MA116-4   1 - 720
      e-tag             721 - 777

<400> SEQUENCE: 4 atg gcc cag gtc caa ctg cag gag tca gga cct gag ctg gtg aag cct         48
Met Ala Gln Val Gln Leu Gln Glu Ser Gly Pro Glu Leu Val Lys Pro
1               5                   10                  15 ggg gct tca gtg aag ata tcc tgc aag gcc tct ggc tac acc ttc act         96
Gly Ala Ser Val Lys Ile Ser Cys Lys Ala Ser Gly Tyr Thr Phe Thr
            20                  25                  30 gac tac cat gtt cac tgg gtg aag ggg aag cct gga cag gga ctt gaa        144
Asp Tyr His Val His Trp Val Lys Gly Lys Pro Gly Gln Gly Leu Glu
        35                  40                  45 tgg att gga atg act tat cct gga ttc gat aat act aat tac agt gag        192
Trp Ile Gly Met Thr Tyr Pro Gly Phe Asp Asn Thr Asn Tyr Ser Glu
    50                  55                  60 act ttc aag ggc aag gcc aca ttg act gta gac aca tcc tcc aac aca        240
Thr Phe Lys Gly Lys Ala Thr Leu Thr Val Asp Thr Ser Ser Asn Thr
65                  70                  75                  80 gtc tac atg cag ctc agc agc ctg aca tct gag gac act gct gtc tat        288
Val Tyr Met Gln Leu Ser Ser Leu Thr Ser Glu Asp Thr Ala Val Tyr
                85                  90                  95 ttt tgt gca aga ggt gtg ggc ctt gac tac tgg ggc caa ggg acc acg        336
Phe Cys Ala Arg Gly Val Gly Leu Asp Tyr Trp Gly Gln Gly Thr Thr
            100                 105                 110 gtc acc gtc tcc tca ggt gga ggc ggt tca ggc gga ggt ggc tct ggc        384
Val Thr Val Ser Ser Gly Gly Gly Gly Ser Gly Gly Gly Gly Ser Gly
        115                 120                 125 ggt ggc gga tcg gca tcg agc tca ctc agt ctc tca aat tcg ttg tcc        432
Gly Gly Gly Ser Ala Ser Ser Ser Leu Ser Leu Ser Asn Ser Leu Ser
    130                 135                 140 aca tca ata gga gac agg atc aga atc acc tgc aag gcc agt cag gat        480
Thr Ser Ile Gly Asp Arg Ile Arg Ile Thr Cys Lys Ala Ser Gln Asp
145                 150                 155                 160 gtg gat act gct gta ggc tgg tat caa cag aga cca ggg caa tct cct        528
Val Asp Thr Ala Val Gly Trp Tyr Gln Gln Arg Pro Gly Gln Ser Pro
                165                 170                 175 aaa cta ctg att ttc tgg tca tcc acc cgg cac act gga gtc cct gat        576
Lys Leu Leu Ile Phe Trp Ser Ser Thr Arg His Thr Gly Val Pro Asp
            180                 185                 190
```

|  |  |
|---|---:|
| cgc ttc aca ggc agt gga tct ggg aca gat ttc act ctc acc att agc<br>Arg Phe Thr Gly Ser Gly Ser Gly Thr Asp Phe Thr Leu Thr Ile Ser<br>     195                   200                 205 | 624 |
| aat gtg cag tct gat gac ttg gca gat tat ttc tgt cac caa tat agc<br>Asn Val Gln Ser Asp Asp Leu Ala Asp Tyr Phe Cys His Gln Tyr Ser<br> 210                   215                 220 | 672 |
| agc tat cca ttc acg ttc ggc tcg ggg aca aag ttg gaa ata aaa cgg<br>Ser Tyr Pro Phe Thr Phe Gly Ser Gly Thr Lys Leu Glu Ile Lys Arg<br>225                 230                235               240 | 720 |
| gcg gcc gca ggt gcg ccg gtg ccg tat ccg gat ccg ctg gaa ccg cgt<br>Ala Ala Ala Gly Ala Pro Val Pro Tyr Pro Asp Pro Leu Glu Pro Arg<br>                   245                 250               255 | 768 |
| gcc gca tag<br>Ala Ala | 777 |

```
<210> SEQ ID NO 5
<211> LENGTH: 777
<212> TYPE: DNA
<213> ORGANISM: mouse
<220> FEATURE:
<221> NAME/KEY: CDS
<222> LOCATION: (1)..(777)
<223> OTHER INFORMATION: scFv protein MA116-14   1 - 720
      e-tag                                   721 - 777

<400> SEQUENCE: 5
```

|  |  |
|---|---:|
| atg gcc cag gtc caa ctg cag gag tca gga cct gag ctg gtg aag cct<br>Met Ala Gln Val Gln Leu Gln Glu Ser Gly Pro Glu Leu Val Lys Pro<br>1                 5                    10                 15 | 48 |
| ggg gct tca gtg aag ata tcc tgc aag gcc tct ggc tac acc ttc act<br>Gly Ala Ser Val Lys Ile Ser Cys Lys Ala Ser Gly Tyr Thr Phe Thr<br>                 20                 25                 30 | 96 |
| gac tac cat gtt cac tgg gtg aag ggg aag cct gga cag gga ctt gaa<br>Asp Tyr His Val His Trp Val Lys Gly Lys Pro Gly Gln Gly Leu Glu<br>                 35                 40                 45 | 144 |
| tgg att gga atg act tat cct gga ttc gat aat act aat tac agt gag<br>Trp Ile Gly Met Thr Tyr Pro Gly Phe Asp Asn Thr Asn Tyr Ser Glu<br>     50                 55                 60 | 192 |
| act ttc aag ggc aag gcc aca ttg act gta gac aca tcc tcc aac aca<br>Thr Phe Lys Gly Lys Ala Thr Leu Thr Val Asp Thr Ser Ser Asn Thr<br>65                 70                 75               80 | 240 |
| gtc tac atg cag ctc agc agc ctg aca tct gag gac acc gct gtc tat<br>Val Tyr Met Gln Leu Ser Ser Leu Thr Ser Glu Asp Thr Ala Val Tyr<br>                 85                 90                 95 | 288 |
| ttt tgt gca aga ggt gtg ggc ctt gac tac tgg ggc caa ggg acc acg<br>Phe Cys Ala Arg Gly Val Gly Leu Asp Tyr Trp Gly Gln Gly Thr Thr<br>                100               105              110 | 336 |
| gtc acc gtc tcc tca ggt gga ggc ggt tca ggc gga ggt ggc tct ggc<br>Val Thr Val Ser Ser Gly Gly Gly Gly Ser Gly Gly Gly Gly Ser Gly<br>              115                 120              125 | 384 |
| ggt ggc gga tcg gac atc gag ctc act cag tct ccc aaa ttc gtt gtc<br>Gly Gly Gly Ser Asp Ile Glu Leu Thr Gln Ser Pro Lys Phe Val Val<br>     130                135                140 | 432 |
| aca tca ata gga gac agg atc aga atc acc tgc aag gcc agt cag gat<br>Thr Ser Ile Gly Asp Arg Ile Arg Ile Thr Cys Lys Ala Ser Gln Asp<br>145                150                155               160 | 480 |
| gtg gat act gct gta ggc tgg tat caa cag aga cca ggg caa tct cct<br>Val Asp Thr Ala Val Gly Trp Tyr Gln Gln Arg Pro Gly Gln Ser Pro<br>                165                 170              175 | 528 |
| aaa cta ctg att ttc tgg tca tcc acc cgg cac act gga gtc cct gat<br>Lys Leu Leu Ile Phe Trp Ser Ser Thr Arg His Thr Gly Val Pro Asp<br>                180                 185              190 | 576 |

-continued

```
cgc ttc aca ggc agt gga tct ggg aca gat ttc act ctc acc att agc    624
Arg Phe Thr Gly Ser Gly Ser Gly Thr Asp Phe Thr Leu Thr Ile Ser
        195                 200                 205 aat gcg cag tct gaa gac ttg gca gat tat ttc tgt cac caa tat agc    672
Asn Ala Gln Ser Glu Asp Leu Ala Asp Tyr Phe Cys His Gln Tyr Ser
    210                 215                 220 agc tat cca ttc acg ttc ggc tcg ggg aca aag ttg gaa ata aaa cgg    720
Ser Tyr Pro Phe Thr Phe Gly Ser Gly Thr Lys Leu Glu Ile Lys Arg
225                 230                 235                 240 gcg gcc gca ggt gcg ccg gtg ccg tat ccg gat ccg ctg gaa ccg cgt    768
Ala Ala Ala Gly Ala Pro Val Pro Tyr Pro Asp Pro Leu Glu Pro Arg
                245                 250                 255 gcc gca tag                                                        777
Ala Ala

<210> SEQ ID NO 6
<211> LENGTH: 777
<212> TYPE: DNA
<213> ORGANISM: mouse
<220> FEATURE:
<221> NAME/KEY: CDS
<222> LOCATION: (1)..(777)
<223> OTHER INFORMATION: scFv protein MA116-16    1 - 720
      e-tag    721 - 777

<400> SEQUENCE: 6 atg gcc cag gtc caa ctg cag gag tca gga cct gag ctg gtg aag tct     48
Met Ala Gln Val Gln Leu Gln Glu Ser Gly Pro Glu Leu Val Lys Ser
1               5                   10                  15 ggg gct tca gtg aag ata tcc tgc aag gcc tct ggc tac acc ttc act     96
Gly Ala Ser Val Lys Ile Ser Cys Lys Ala Ser Gly Tyr Thr Phe Thr
            20                  25                  30 gac tac cat gtt cac tgg gtg aag ggg aag cct gga cag gga ctt gaa    144
Asp Tyr His Val His Trp Val Lys Gly Lys Pro Gly Gln Gly Leu Glu
        35                  40                  45 tgg att gga atg act tat cct gga ttc gat aat act aat tac agt gag    192
Trp Ile Gly Met Thr Tyr Pro Gly Phe Asp Asn Thr Asn Tyr Ser Glu
    50                  55                  60 act ttc aag ggc aag gcc aca ttg act gta gac aca tcc tcc aac aca    240
Thr Phe Lys Gly Lys Ala Thr Leu Thr Val Asp Thr Ser Ser Asn Thr
65                  70                  75                  80 gtc tac atg cag ctc agc agc ctg aca tct gag gac acc gct gtc tat    288
Val Tyr Met Gln Leu Ser Ser Leu Thr Ser Glu Asp Thr Ala Val Tyr
            85                  90                  95 ttt tgt gca aga ggt gtg ggc ctt gac tac tgg ggc caa ggg acc acg    336
Phe Cys Ala Arg Gly Val Gly Leu Asp Tyr Trp Gly Gln Gly Thr Thr
                100                 105                 110 gtc acc gtc tcc tca ggt ggg ggc ggt tca ggc gga ggt ggc tct ggc    384
Val Thr Val Ser Ser Gly Gly Gly Gly Ser Gly Gly Gly Gly Ser Gly
            115                 120                 125 ggt ggc gga tcg gac atc gag ctc act cag tct cca aat tcg ttg tcc    432
Gly Gly Gly Ser Asp Ile Glu Leu Thr Gln Ser Pro Asn Ser Leu Ser
        130                 135                 140 aca tca ata gga gac agg atc aga atc acc tgc aag gcc agt cag gat    480
Thr Ser Ile Gly Asp Arg Ile Arg Ile Thr Cys Lys Ala Ser Gln Asp
145                 150                 155                 160 gtg gat act gct gta ggc tgg tat caa cag aga cca ggg caa tct cct    528
Val Asp Thr Ala Val Gly Trp Tyr Gln Gln Arg Pro Gly Gln Ser Pro
            165                 170                 175 aaa cta ctg att ttc tgg tca tcc acc cgg cac act gga gtc cct gac    576
Lys Leu Leu Ile Phe Trp Ser Ser Thr Arg His Thr Gly Val Pro Asp
```

-continued

```
                   180                 185                 190
cgc ttc aca ggc agt gga tct gga aca gat ttc act ctc acc att agc        624
Arg Phe Thr Gly Ser Gly Ser Gly Thr Asp Phe Thr Leu Thr Ile Ser
            195                 200                 205 aat gtg cag tct gaa gac ttg gca gat tat ttc tgt cac caa tat agc        672
Asn Val Gln Ser Glu Asp Leu Ala Asp Tyr Phe Cys His Gln Tyr Ser
    210                 215                 220 agc tat cca ttc acg ttc ggc tcg gga aca aag ttg gaa ata aaa cgg        720
Ser Tyr Pro Phe Thr Phe Gly Ser Gly Thr Lys Leu Glu Ile Lys Arg
225                 230                 235                 240 gcg gcc gca ggt gcg ccg gtg ccg tat ccg gat ccg ctg gaa ccg cgt        768
Ala Ala Ala Gly Ala Pro Val Pro Tyr Pro Asp Pro Leu Glu Pro Arg
                245                 250                 255 gcc gca tag                                                            777
Ala Ala <210> SEQ ID NO 7
<211> LENGTH: 777
<212> TYPE: DNA
<213> ORGANISM: mouse
<220> FEATURE:
<221> NAME/KEY: CDS
<222> LOCATION: (1)..(777)
<223> OTHER INFORMATION: scFv protein MA116-15  1 - 720
      e-tag            721 - 777

<400> SEQUENCE: 7 atg gcc cag gtc caa ctg cag gag tca gga cct gag ctg gtg aag cct        48
Met Ala Gln Val Gln Leu Gln Glu Ser Gly Pro Glu Leu Val Lys Pro
1               5                   10                  15 ggg gct tca gtg aag ata tcc tgc aag gcc tct ggc tac acc ttc act        96
Gly Ala Ser Val Lys Ile Ser Cys Lys Ala Ser Gly Tyr Thr Phe Thr
            20                  25                  30 gac tac cat gtt cac tgg gtg aag ggg aag cct gga cag gga ctt gaa        144
Asp Tyr His Val His Trp Val Lys Gly Lys Pro Gly Gln Gly Leu Glu
        35                  40                  45 tgg att gga atg act tat cct gga ttc gat aat act aat tac agt gag        192
Trp Ile Gly Met Thr Tyr Pro Gly Phe Asp Asn Thr Asn Tyr Ser Glu
    50                  55                  60 act ttc aag ggc aag gcc aca ttg act gta gac aca tcc tcc aac aca        240
Thr Phe Lys Gly Lys Ala Thr Leu Thr Val Asp Thr Ser Ser Asn Thr
65                  70                  75                  80 gtc tac atg cag ctc agc agc ctg aca tct gag gac acc gct gtc tat        288
Val Tyr Met Gln Leu Ser Ser Leu Thr Ser Glu Asp Thr Ala Val Tyr
                85                  90                  95 ttt tgt gca aga ggt gtg ggc ctt gac tac tgg ggc caa ggg acc acg        336
Phe Cys Ala Arg Gly Val Gly Leu Asp Tyr Trp Gly Gln Gly Thr Thr
            100                 105                 110 gtc acc gtc tcc tca ggt gga ggc ggt tca ggc gga ggt ggc tct ggc        384
Val Thr Val Ser Ser Gly Gly Gly Gly Ser Gly Gly Gly Gly Ser Gly
        115                 120                 125 ggt ggc gga tcg gac atc gag ctc act cag tct cca aat tcg ttg tcc        432
Gly Gly Gly Ser Asp Ile Glu Leu Thr Gln Ser Pro Asn Ser Leu Ser
    130                 135                 140 aca tca ata gga gac agg atc aga atc acc tgc aag gcc agt cag gat        480
Thr Ser Ile Gly Asp Arg Ile Arg Ile Thr Cys Lys Ala Ser Gln Asp
145                 150                 155                 160 gtg gat act gct gta ggc tgg tat caa cag aga cca ggg caa tct cct        528
Val Asp Thr Ala Val Gly Trp Tyr Gln Gln Arg Pro Gly Gln Ser Pro
                165                 170                 175 aaa cta ctg att ttc tgg tca tcc acc cgg cac act gga gtc cct gat        576
```

```
Lys Leu Leu Ile Phe Trp Ser Ser Thr Arg His Thr Gly Val Pro Asp
                180                 185                 190 cgc ttc aca ggc agt gga tct ggg aca gat ttc act ctc acc att agc    624
Arg Phe Thr Gly Ser Gly Ser Gly Thr Asp Phe Thr Leu Thr Ile Ser
        195                 200                 205 aat gtg cag tct gaa gac ttg gca gat tat ttc tgt cac caa tat agc    672
Asn Val Gln Ser Glu Asp Leu Ala Asp Tyr Phe Cys His Gln Tyr Ser
    210                 215                 220 agc tat cca ttc acg ttc ggc tcg ggg aca aag ttg gaa ata aaa cgg    720
Ser Tyr Pro Phe Thr Phe Gly Ser Gly Thr Lys Leu Glu Ile Lys Arg
225                 230                 235                 240 gcg gcc gca ggt gcg ccg gtg ccg tat ccg gat ccg ctg gaa ccg cgt    768
Ala Ala Ala Gly Ala Pro Val Pro Tyr Pro Asp Pro Leu Glu Pro Arg
                245                 250                 255 gcc gca tag                                                          777
Ala Ala <210> SEQ ID NO 8
<211> LENGTH: 117
<212> TYPE: PRT
<213> ORGANISM: mouse

<400> SEQUENCE: 8

Met Ala Gln Val Gln Leu Gln Glu Ser Gly Pro Glu Leu Val Lys Pro
1               5                   10                  15

Gly Ala Ser Val Lys Ile Ser Cys Lys Ala Ser Gly Tyr Thr Phe Thr
                20                  25                  30

Asp Tyr His Val His Trp Val Lys Gly Lys Pro Gly Gln Gly Leu Glu
            35                  40                  45

Trp Ile Gly Met Thr Tyr Pro Gly Phe Asp Asn Thr Asn Tyr Ser Glu
        50                  55                  60

Thr Phe Lys Gly Lys Ala Thr Leu Thr Val Asp Thr Phe Ser Thr Thr
65                  70                  75                  80

Val Tyr Met Gln Leu Ser Ser Leu Thr Ser Glu Asp Thr Val Val Tyr
                85                  90                  95

Phe Cys Ala Arg Gly Val Gly Leu Asp Tyr Trp Gly Gln Gly Thr Thr
            100                 105                 110

Val Thr Val Ser Ser
        115

<210> SEQ ID NO 9
<211> LENGTH: 120
<212> TYPE: PRT
<213> ORGANISM: mouse

<400> SEQUENCE: 9

Met Ala Gln Val Gln Leu Gln Gln Ser Gly Ala Glu Leu Val Arg Pro
1               5                   10                  15

Gly Ala Ser Val Thr Leu Ser Cys Lys Ala Ser Asp Tyr Thr Phe Thr
                20                  25                  30

Asp Tyr Glu Met His Trp Val Lys Gln Thr Pro Val His Gly Leu Lys
            35                  40                  45

Trp Ile Gly Ala Ile Asp Pro Glu Thr Gly Gly Thr Ala Tyr Asn Gln
        50                  55                  60

Lys Phe Lys Gly Arg Ala Thr Leu Thr Ala Asp Lys Ser Ser Thr Thr
65                  70                  75                  80

Ala Tyr Met Glu Leu Arg Ser Leu Thr Ser Glu Asp Ser Ala Val Tyr
                85                  90                  95
```

-continued

Tyr Cys Thr Arg Tyr Tyr Gly Asn Pro Trp Pro Ala Tyr Trp Gly Gln
            100                 105                 110

Gly Thr Thr Val Thr Val Ser Ser
        115                 120

<210> SEQ ID NO 10
<211> LENGTH: 122
<212> TYPE: PRT
<213> ORGANISM: mouse

<400> SEQUENCE: 10

His Ser Gln Val Gln Leu Gln Gln Pro Gly Ala Glu Leu Val Lys Pro
1               5                   10                  15

Gly Ala Ser Val Lys Leu Ser Cys Lys Ala Ser Gly Tyr Thr Phe Thr
            20                  25                  30

Ser Tyr Trp Met His Trp Val Lys Gln Arg Pro Gly Arg Gly Leu Glu
        35                  40                  45

Trp Ile Gly Arg Ile Asp Pro Asn Ser Gly Gly Thr Lys Tyr Asn Glu
    50                  55                  60

Lys Phe Lys Ser Lys Ala Thr Leu Thr Val Asp Lys Pro Ser Ser Thr
65                  70                  75                  80

Ala Tyr Met Gln Leu Ser Ser Leu Thr Ser Glu Asp Ser Ala Val Tyr
                85                  90                  95

Tyr Cys Ala Arg Tyr Asp Tyr Tyr Gly Ser Ser Tyr Phe Asp Tyr Trp
            100                 105                 110

Gly Gln Gly Thr Thr Leu Thr Val Ser Ser
        115                 120

<210> SEQ ID NO 11
<211> LENGTH: 122
<212> TYPE: PRT
<213> ORGANISM: mouse

<400> SEQUENCE: 11

Asp Gly Gln Val Gln Leu Gln Gln Pro Gly Ala Glu Leu Val Lys Pro
1               5                   10                  15

Gly Ala Ser Val Lys Leu Ser Cys Lys Ala Ser Gly Tyr Thr Phe Thr
            20                  25                  30

Ser Tyr Trp Met His Trp Val Lys Gln Arg Pro Gly Arg Gly Leu Glu
        35                  40                  45

Trp Ile Gly Arg Ile Asp Pro Asn Ser Gly Gly Thr Lys Tyr Asn Glu
    50                  55                  60

Lys Phe Lys Ser Lys Ala Thr Leu Thr Val Asp Lys Pro Ser Ser Thr
65                  70                  75                  80

Ala Tyr Met Gln Leu Ser Ser Leu Thr Ser Glu Asp Ser Ala Val Tyr
                85                  90                  95

Tyr Cys Ala Arg Tyr Asp Tyr Tyr Gly Ser Ser Tyr Phe Asp Tyr Trp
            100                 105                 110

Gly Gln Gly Thr Thr Leu Thr Val Ser Ser
        115                 120

<210> SEQ ID NO 12
<211> LENGTH: 120
<212> TYPE: PRT
<213> ORGANISM: mouse

<400> SEQUENCE: 12

-continued

```
Glu Val Gln Leu Gln Gln Ser Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
            35                  40                  45

Gly Glu Ile Asp Pro Ser Asp Ser Tyr Thr Tyr Tyr Asn Gln Lys Phe
50                      55                  60

Lys Gly Lys Ala Thr Leu Thr Val Asp Lys Ser Ser Ser Thr Ala Tyr
65                  70                  75                  80

Met Gln Phe Ser Ser Leu Thr Ser Glu Asp Ser Ala Val Tyr Tyr Cys
                85                  90                  95

Ala Arg Arg Tyr Tyr Gly Ser Arg Val Ser Met Asp Tyr Trp Gly Gln
                100                 105                 110

Gly Thr Ser Val Thr Val Ser Ser
        115                 120

<210> SEQ ID NO 13
<211> LENGTH: 110
<212> TYPE: PRT
<213> ORGANISM: mouse

<400> SEQUENCE: 13

Asp Ser Ser Ser Leu Val Ser Lys Phe Val Ser Thr Ser Ile Gly Asp
1               5                   10                  15

Arg Ile Arg Ile Thr Cys Lys Ala Ser Gln Asp Val Asp Thr Ala Val
            20                  25                  30

Gly Trp Tyr Gln Gln Arg Pro Gly Gln Ser Pro Lys Leu Leu Ile Phe
            35                  40                  45

Trp Ser Ser Thr Arg His Thr Gly Val Pro Asp Arg Phe Thr Gly Ser
        50                  55                  60

Gly Ser Gly Thr Asp Phe Thr Leu Thr Ile Ser Asn Val Gln Ser Glu
65                  70                  75                  80

Asp Leu Ala Asp Tyr Phe Cys His Gln Tyr Ser Ser His Pro Phe Thr
                85                  90                  95

Phe Gly Ser Gly Thr Lys Leu Glu Ile Lys Arg Ala Ala Ala
                100                 105                 110

<210> SEQ ID NO 14
<211> LENGTH: 110
<212> TYPE: PRT
<213> ORGANISM: mouse

<400> SEQUENCE: 14

Asp Ile Glu Leu Thr Gln Ser Pro Ala Ser Leu Ser Val Ser Val Gly
1               5                   10                  15

Glu Thr Val Thr Ile Thr Cys Arg Ala Ser Glu Asn Ile Tyr Arg Asn
            20                  25                  30

Leu Ala Trp Tyr Gln Gln Lys Gln Gly Lys Ser Pro Gln Leu Leu Val
            35                  40                  45

Tyr Ala Ala Thr Asn Leu Ala Asp Gly Val Pro Ser Arg Phe Ser Gly
50                  55                  60

Ser Gly Ser Gly Thr Gln Tyr Ser Leu Lys Ile Asn Ser Leu Lys Ser
65                  70                  75                  80

Glu Asp Phe Gly Ser Tyr Tyr Cys Gln His Phe Trp Gly Thr Pro Tyr
                85                  90                  95
```

Thr Phe Gly Gly Gly Thr Lys Leu Glu Ile Lys Arg Ala Ala
            100                 105                 110

<210> SEQ ID NO 15
<211> LENGTH: 106
<212> TYPE: PRT
<213> ORGANISM: mouse

<400> SEQUENCE: 15

Asp Ile Gln Met Thr Gln Ser Pro Ala Ser Leu Ser Ala Ser Val Gly
1               5                   10                  15

Glu Thr Val Thr Ile Thr Cys Arg Ala Ser Glu Asn Ile Tyr Ser Tyr
            20                  25                  30

Leu Ala Trp Tyr Gln Gln Lys Gln Gly Lys Ser Pro Gln Leu Leu Val
        35                  40                  45

Tyr Asn Ala Lys Thr Leu Ala Glu Gly Val Pro Ser Arg Phe Ser Gly
    50                  55                  60

Ser Gly Ser Gly Thr Gln Phe Ser Leu Lys Ile Asn Ser Leu Gln Pro
65                  70                  75                  80

Glu Asp Phe Gly Ser Tyr Tyr Cys Gln His His Tyr Gly Thr Pro Phe
                85                  90                  95

Thr Phe Gly Ser Gly Thr Lys Leu Glu Ile
            100                 105

<210> SEQ ID NO 16
<211> LENGTH: 110
<212> TYPE: PRT
<213> ORGANISM: mouse

<400> SEQUENCE: 16

Asp Ile Gln Met Thr Gln Ser Pro Ala Ser Leu Ser Ala Ser Val Gly
1               5                   10                  15

Glu Thr Val Thr Ile Ile Cys Arg Ala Ser Val Asn Ile Tyr Ser Tyr
            20                  25                  30

Leu Ala Trp Tyr Gln Gln Lys Gln Gly Lys Ser Pro Gln Leu Leu Val
        35                  40                  45

Tyr Asn Ala Lys Ile Leu Ala Glu Gly Val Pro Ser Arg Phe Ser Gly
    50                  55                  60

Ser Gly Ser Gly Thr Gln Phe Ser Leu Lys Ile Asn Ser Leu Gln Pro
65                  70                  75                  80

Glu Asp Phe Gly Ser Tyr Tyr Cys Gln His His Tyr Gly Pro Phe Thr
                85                  90                  95

Phe Gly Ser Gly Thr Lys Leu Glu Ile Lys Arg Ala Asp Ala
            100                 105                 110

<210> SEQ ID NO 17
<211> LENGTH: 108
<212> TYPE: PRT
<213> ORGANISM: mouse

<400> SEQUENCE: 17

Asp Ile Gln Met Thr Gln Ser Pro Ala Ser Leu Ser Ala Ser Val Gly
1               5                   10                  15

Glu Thr Val Thr Ile Thr Cys Arg Ala Ser Gly Asn Ile His Asn Tyr
            20                  25                  30

Leu Ala Trp Tyr Gln Gln Lys Pro Gly Lys Ser Pro Gln Leu Leu Val
        35                  40                  45

Tyr Asn Ala Lys Thr Leu Ala Asp Gly Val Pro Ser Arg Phe Ser Gly

```
                50                  55                  60
Ser Gly Ser Gly Thr Gln Tyr Ser Leu Lys Ile Asn Ser Leu Gln Pro
 65                  70                  75                  80

Glu Asp Phe Gly Ser Tyr Tyr Cys Gln His Phe Trp Ser Thr Pro Trp
                     85                  90                  95

Thr Phe Gly Gly Gly Thr Lys Leu Glu Ile Lys Arg
                100                 105

<210> SEQ ID NO 18
<211> LENGTH: 101
<212> TYPE: PRT
<213> ORGANISM: mouse

<400> SEQUENCE: 18

Pro Ala Ser Leu Ser Ala Ser Val Gly Glu Thr Cys Thr Ile Thr Cys
  1               5                  10                  15

Arg Ala Ser Glu Asn Ile Tyr Ser Tyr Leu Ala Trp Tyr Gln Gln Lys
                 20                  25                  30

Gln Gly Lys Ser Pro Gln Leu Leu Val Tyr Asn Ala Lys Thr Leu Ala
             35                  40                  45

Glu Gly Val Pro Ser Arg Phe Ser Gly Ser Gly Ser Gly Thr Gln Phe
 50                  55                  60

Ser Leu Lys Ile Asn Ser Leu Gln Pro Glu Asp Phe Gly Arg Tyr Tyr
 65                  70                  75                  80

Cys Gln His Val Tyr Gly Thr Pro Tyr Thr Phe Gly Gly Gly Thr Lys
                 85                  90                  95

Leu Glu Ile Lys Arg
            100

<210> SEQ ID NO 19
<211> LENGTH: 108
<212> TYPE: PRT
<213> ORGANISM: mouse

<400> SEQUENCE: 19

Asp Ile Gln Met Thr Gln Ser Pro Ala Ser Leu Ser Ala Ser Val Gly
  1               5                  10                  15

Glu Thr Val Thr Ile Thr Cys Arg Ala Ser Glu Asn Thr Tyr Ser Tyr
                 20                  25                  30

Leu Ala Trp Tyr Gln Gln Lys Gln Gly Lys Ser Pro Gln Leu Leu Val
             35                  40                  45

Tyr Asn Ala Lys Thr Leu Ala Glu Gly Val Pro Ser Arg Phe Ser Gly
         50                  55                  60

Ser Gly Ser Gly Thr Gln Phe Ser Leu Lys Ile Asn Ser Leu Gln Pro
 65                  70                  75                  80

Glu Asp Phe Gly Ser Tyr Tyr Cys Gln His His Tyr Gly Thr Pro Phe
                     85                  90                  95

Thr Phe Gly Ser Gly Thr Lys Leu Glu Ile Lys Arg
                100                 105

<210> SEQ ID NO 20
<211> LENGTH: 39
<212> TYPE: DNA
<213> ORGANISM: mouse

<400> SEQUENCE: 20
acatcgagct cactcagtct ccaaattcgt gtccacatc                        39
```

```
<210> SEQ ID NO 21
<211> LENGTH: 40
<212> TYPE: DNA
<213> ORGANISM: mouse

<400> SEQUENCE: 21
acatcgagct cactcaatct ccatcctcct tatctgcctc            40

<210> SEQ ID NO 22
<211> LENGTH: 40
<212> TYPE: DNA
<213> ORGANISM: mouse

<400> SEQUENCE: 22
acatcgagct cactcagtct ccatcctcct tatctgcctc            40

<210> SEQ ID NO 23
<211> LENGTH: 39
<212> TYPE: DNA
<213> ORGANISM: mouse

<400> SEQUENCE: 23
acatcgagct cactcagtct ccaaattcgt gtccacatc             39

<210> SEQ ID NO 24
<211> LENGTH: 39
<212> TYPE: DNA
<213> ORGANISM: mouse

<400> SEQUENCE: 24
acatcgagct cactcagtct ccaaattcgt gtccacatc             39

<210> SEQ ID NO 25
<211> LENGTH: 37
<212> TYPE: DNA
<213> ORGANISM: mouse

<400> SEQUENCE: 25
actcgagctc actcgtctcc aaattcgtgt ccacatc               37

<210> SEQ ID NO 26
<211> LENGTH: 37
<212> TYPE: DNA
<213> ORGANISM: mouse

<400> SEQUENCE: 26
gactcgagct cactcgtcct ccaaattcgt gtccaca               37

<210> SEQ ID NO 27
<211> LENGTH: 37
<212> TYPE: DNA
<213> ORGANISM: mouse

<400> SEQUENCE: 27
gactcgagct cactcgtcct ccaaattcgt gtccaca               37

<210> SEQ ID NO 28
<211> LENGTH: 40
<212> TYPE: DNA
<213> ORGANISM: mouse

<400> SEQUENCE: 28
gcatcgagct cactcagtcc tctcaaattc gttgtccaca            40
```

-continued

<210> SEQ ID NO 29
<211> LENGTH: 40
<212> TYPE: DNA
<213> ORGANISM: mouse

<400> SEQUENCE: 29
gacatcgagc tcactcagtc ctcccaaatt cgttgtcaca                          40

<210> SEQ ID NO 30
<211> LENGTH: 40
<212> TYPE: DNA
<213> ORGANISM: mouse

<400> SEQUENCE: 30
gacatcgagc tcactcagtc ctccaaattc gttgtccaca                          40

<210> SEQ ID NO 31
<211> LENGTH: 40
<212> TYPE: DNA
<213> ORGANISM: mouse

<400> SEQUENCE: 31
gacatcgagc tcactcagtc ctccaaattc gttgtccaca                          40

<210> SEQ ID NO 32
<211> LENGTH: 239
<212> TYPE: PRT
<213> ORGANISM: mouse

<400> SEQUENCE: 32

Met Ala Gln Val Gln Leu Gln Glu Ser Gly Pro Glu Leu Val Lys Pro
1               5                   10                  15

Gly Ala Ser Val Lys Ile Ser Cys Lys Ala Ser Gly Tyr Thr Phe Thr
                20                  25                  30

Asp Tyr His Val His Trp Val Lys Gly Lys Pro Gly Gln Gly Leu Glu
            35                  40                  45

Trp Ile Gly Met Thr Tyr Pro Gly Phe Asp Asn Thr Asn Tyr Ser Glu
        50                  55                  60

Thr Phe Lys Gly Lys Ala Thr Leu Thr Val Asp Thr Phe Ser Thr Thr
65                  70                  75                  80

Val Tyr Met Gln Leu Ser Ser Leu Thr Ser Glu Asp Thr Val Val Tyr
                85                  90                  95

Phe Cys Ala Arg Gly Val Gly Leu Asp Tyr Trp Gly Gln Gly Thr Thr
                100                 105                 110

Val Thr Val Ser Ser Gly Gly Gly Ser Gly Gly Gly Gly Ser Gly
            115                 120                 125

Gly Gly Gly Ser Asp Ser Ser Leu Val Ser Lys Phe Val Ser Thr
        130                 135                 140

Ser Ile Gly Asp Arg Ile Arg Ile Thr Cys Lys Ala Ser Gln Asp Val
145                 150                 155                 160

Asp Thr Ala Val Gly Trp Tyr Gln Gln Arg Pro Gly Gln Ser Pro Lys
                165                 170                 175

Leu Leu Ile Phe Trp Ser Ser Thr Arg His Thr Gly Val Pro Asp Arg
            180                 185                 190

Phe Thr Gly Ser Gly Ser Gly Thr Asp Phe Thr Leu Thr Ile Ser Asn
        195                 200                 205

Val Gln Ser Glu Asp Leu Ala Asp Tyr Phe Cys His Gln Tyr Ser Ser

His Pro Phe Thr Phe Gly Ser Gly Thr Lys Leu Glu Ile Lys Arg
225                 230                 235

<210> SEQ ID NO 33
<211> LENGTH: 239
<212> TYPE: PRT
<213> ORGANISM: mouse

<400> SEQUENCE: 33

Met Ala Gln Val Gln Leu Gln Glu Ser Gly Pro Glu Leu Val Lys Pro
1               5                   10                  15

Gly Ala Ser Val Lys Ile Ser Cys Lys Ala Ser Gly Tyr Thr Phe Thr
                20                  25                  30

Asp Tyr His Val His Trp Val Lys Gly Lys Pro Gly Gln Gly Leu Glu
            35                  40                  45

Trp Ile Gly Met Thr Tyr Pro Gly Phe Asp Asp Thr Asn Tyr Ser Glu
    50                  55                  60

Thr Phe Lys Gly Lys Ala Thr Leu Thr Val Asp Thr Ser Ser Asn Thr
65                  70                  75                  80

Val Tyr Met Gln Leu Ser Ser Leu Thr Ser Glu Asp Thr Ala Val Tyr
                85                  90                  95

Phe Cys Ala Arg Gly Val Gly Leu Asp Tyr Trp Gly Gln Gly Thr Thr
            100                 105                 110

Val Thr Val Ser Ser Gly Gly Gly Ser Gly Gly Gly Ser Gly
        115                 120                 125

Gly Gly Gly Ser Asp Ser Ser Leu Val Ser Lys Phe Val Ser Thr
    130                 135                 140

Ser Ile Gly Asp Arg Ile Arg Ile Thr Cys Lys Ala Ser Gln Asp Val
145                 150                 155                 160

Asp Thr Ala Val Gly Trp Tyr Gln Gln Arg Pro Gly Gln Ser Pro Lys
                165                 170                 175

Leu Leu Ile Phe Trp Ser Ser Thr Arg His Thr Gly Val Pro Asp Arg
            180                 185                 190

Phe Thr Gly Ser Gly Ser Gly Thr Asp Phe Thr Leu Thr Ile Ser Asn
    195                 200                 205

Val Gln Ser Glu Asp Leu Ala Asp Tyr Phe Cys His Gln Tyr Ser Ser
        210                 215                 220

Tyr Pro Phe Thr Phe Gly Ser Gly Thr Lys Leu Glu Ile Lys Arg
225                 230                 235

<210> SEQ ID NO 34
<211> LENGTH: 240
<212> TYPE: PRT
<213> ORGANISM: mouse

<400> SEQUENCE: 34

Met Ala Gln Val Gln Leu Gln Glu Ser Gly Pro Glu Leu Val Lys Pro
1               5                   10                  15

Gly Ala Ser Val Lys Ile Ser Cys Lys Ala Ser Gly Tyr Thr Phe Thr
                20                  25                  30

Asp Tyr His Val His Trp Val Lys Gly Lys Pro Gly Gln Gly Leu Glu
            35                  40                  45

Trp Ile Gly Met Thr Tyr Pro Gly Phe Asp Asn Thr Asn Tyr Ser Glu
    50                  55                  60

Thr Phe Lys Gly Lys Ala Thr Leu Thr Val Asp Thr Ser Ser Asn Thr

-continued

```
                65                  70                  75                  80
Val Tyr Met Gln Leu Ser Ser Leu Thr Ser Glu Asp Thr Ala Val Tyr
                    85                  90                  95

Phe Cys Ala Arg Gly Val Gly Leu Asp Tyr Trp Gly Gln Gly Thr Thr
                    100                 105                 110

Val Thr Val Ser Ser Gly Gly Gly Ser Gly Gly Gly Gly Ser Gly
                    115                 120                 125

Gly Gly Gly Ser Ala Ser Ser Leu Ser Leu Ser Asn Ser Leu Ser
                    130                 135                 140

Thr Ser Ile Gly Asp Arg Ile Arg Ile Thr Cys Lys Ala Ser Gln Asp
145                 150                 155                 160

Val Asp Thr Ala Val Gly Trp Tyr Gln Gln Arg Pro Gly Gln Ser Pro
                    165                 170                 175

Lys Leu Leu Ile Phe Trp Ser Ser Thr Arg His Thr Gly Val Pro Asp
                    180                 185                 190

Arg Phe Thr Gly Ser Gly Ser Gly Thr Asp Phe Thr Leu Thr Ile Ser
                    195                 200                 205

Asn Val Gln Ser Asp Asp Leu Ala Asp Tyr Phe Cys His Gln Tyr Ser
210                 215                 220

Ser Tyr Pro Phe Thr Phe Gly Ser Gly Thr Lys Leu Glu Ile Lys Arg
225                 230                 235                 240

<210> SEQ ID NO 35
<211> LENGTH: 240
<212> TYPE: PRT
<213> ORGANISM: mouse

<400> SEQUENCE: 35

Met Ala Gln Val Gln Leu Gln Glu Ser Gly Pro Glu Leu Val Lys Pro
1                   5                   10                  15

Gly Ala Ser Val Lys Ile Ser Cys Lys Ala Ser Gly Tyr Thr Phe Thr
                    20                  25                  30

Asp Tyr His Val His Trp Val Lys Gly Lys Pro Gly Gln Gly Leu Glu
                    35                  40                  45

Trp Ile Gly Met Thr Tyr Pro Gly Phe Asp Asn Thr Asn Tyr Ser Glu
                    50                  55                  60

Thr Phe Lys Gly Lys Ala Thr Leu Thr Val Asp Thr Ser Ser Asn Thr
65                  70                  75                  80

Val Tyr Met Gln Leu Ser Ser Leu Thr Ser Glu Asp Thr Ala Val Tyr
                    85                  90                  95

Phe Cys Ala Arg Gly Val Gly Leu Asp Tyr Trp Gly Gln Gly Thr Thr
                    100                 105                 110

Val Thr Val Ser Ser Gly Gly Gly Ser Gly Gly Gly Gly Ser Gly
                    115                 120                 125

Gly Gly Gly Ser Asp Ile Glu Leu Thr Gln Ser Pro Lys Phe Val Val
                    130                 135                 140

Thr Ser Ile Gly Asp Arg Ile Arg Ile Thr Cys Lys Ala Ser Gln Asp
145                 150                 155                 160

Val Asp Thr Ala Val Gly Trp Tyr Gln Gln Arg Pro Gly Gln Ser Pro
                    165                 170                 175

Lys Leu Leu Ile Phe Trp Ser Ser Thr Arg His Thr Gly Val Pro Asp
                    180                 185                 190

Arg Phe Thr Gly Ser Gly Ser Gly Thr Asp Phe Thr Leu Thr Ile Ser
                    195                 200                 205
```

```
Asn Ala Gln Ser Glu Asp Leu Ala Asp Tyr Phe Cys His Gln Tyr Ser
            210                 215                 220

Ser Tyr Pro Phe Thr Phe Gly Ser Gly Thr Lys Leu Glu Ile Lys Arg
225                 230                 235                 240

<210> SEQ ID NO 36
<211> LENGTH: 240
<212> TYPE: PRT
<213> ORGANISM: mouse

<400> SEQUENCE: 36

Met Ala Gln Val Gln Leu Gln Glu Ser Gly Pro Glu Leu Val Lys Ser
1               5                   10                  15

Gly Ala Ser Val Lys Ile Ser Cys Lys Ala Ser Gly Tyr Thr Phe Thr
                20                  25                  30

Asp Tyr His Val His Trp Val Lys Gly Lys Pro Gly Gln Gly Leu Glu
            35                  40                  45

Trp Ile Gly Met Thr Tyr Pro Gly Phe Asp Asn Thr Asn Tyr Ser Glu
50                  55                  60

Thr Phe Lys Gly Lys Ala Thr Leu Thr Val Asp Thr Ser Ser Asn Thr
65                  70                  75                  80

Val Tyr Met Gln Leu Ser Ser Leu Thr Ser Glu Asp Thr Ala Val Tyr
                85                  90                  95

Phe Cys Ala Arg Gly Val Gly Leu Asp Tyr Trp Gln Gly Thr Thr
            100                 105                 110

Val Thr Val Ser Ser Gly Gly Gly Ser Gly Gly Gly Ser Gly
            115                 120                 125

Gly Gly Gly Ser Asp Ile Glu Leu Thr Gln Ser Pro Asn Ser Leu Ser
130                 135                 140

Thr Ser Ile Gly Asp Arg Ile Arg Ile Thr Cys Lys Ala Ser Gln Asp
145                 150                 155                 160

Val Asp Thr Ala Val Gly Trp Tyr Gln Gln Arg Pro Gly Gln Ser Pro
                165                 170                 175

Lys Leu Leu Ile Phe Trp Ser Ser Thr Arg His Thr Gly Val Pro Asp
            180                 185                 190

Arg Phe Thr Gly Ser Gly Ser Gly Thr Asp Phe Thr Leu Thr Ile Ser
        195                 200                 205

Asn Val Gln Ser Glu Asp Leu Ala Asp Tyr Phe Cys His Gln Tyr Ser
    210                 215                 220

Ser Tyr Pro Phe Thr Phe Gly Ser Gly Thr Lys Leu Glu Ile Lys Arg
225                 230                 235                 240

<210> SEQ ID NO 37
<211> LENGTH: 240
<212> TYPE: PRT
<213> ORGANISM: mouse

<400> SEQUENCE: 37

Met Ala Gln Val Gln Leu Gln Glu Ser Gly Pro Glu Leu Val Lys Pro
1               5                   10                  15

Gly Ala Ser Val Lys Ile Ser Cys Lys Ala Ser Gly Tyr Thr Phe Thr
                20                  25                  30

Asp Tyr His Val His Trp Val Lys Gly Lys Pro Gly Gln Gly Leu Glu
            35                  40                  45

Trp Ile Gly Met Thr Tyr Pro Gly Phe Asp Asn Thr Asn Tyr Ser Glu
50                  55                  60
```

```
Thr Phe Lys Gly Lys Ala Thr Leu Thr Val Asp Thr Ser Ser Asn Thr
 65                  70                  75                  80

Val Tyr Met Gln Leu Ser Ser Leu Thr Ser Glu Asp Thr Ala Val Tyr
                 85                  90                  95

Phe Cys Ala Arg Gly Val Gly Leu Asp Tyr Trp Gly Gln Gly Thr Thr
                100                 105                 110

Val Thr Val Ser Ser Gly Gly Gly Gly Ser Gly Gly Gly Gly Ser Gly
            115                 120                 125

Gly Gly Gly Ser Asp Ile Glu Leu Thr Gln Ser Pro Asn Ser Leu Ser
130                 135                 140

Thr Ser Ile Gly Asp Arg Ile Arg Ile Thr Cys Lys Ala Ser Gln Asp
145                 150                 155                 160

Val Asp Thr Ala Val Gly Trp Tyr Gln Gln Arg Pro Gly Gln Ser Pro
                165                 170                 175

Lys Leu Leu Ile Phe Trp Ser Ser Thr Arg His Thr Gly Val Pro Asp
                180                 185                 190

Arg Phe Thr Gly Ser Gly Ser Gly Thr Asp Phe Thr Leu Thr Ile Ser
            195                 200                 205

Asn Val Gln Ser Glu Asp Leu Ala Asp Tyr Phe Cys His Gln Tyr Ser
            210                 215                 220

Ser Tyr Pro Phe Thr Phe Gly Ser Gly Thr Lys Leu Glu Ile Lys Arg
225                 230                 235                 240

<210> SEQ ID NO 38
<211> LENGTH: 20
<212> TYPE: DNA
<213> ORGANISM: Artificial
<220> FEATURE:
<223> OTHER INFORMATION: DNA Primer

<400> SEQUENCE: 38
caaattcgtt gtccacatca                                          20

<210> SEQ ID NO 39
<211> LENGTH: 28
<212> TYPE: DNA
<213> ORGANISM: Artificial
<220> FEATURE:
<223> OTHER INFORMATION: DNA Primer

<400> SEQUENCE: 39
gagactgagt gagctcgatg tccgatcc                                 28
```

CLONING, EXPRESSION, SEQUENCING, AND FUNCTIONAL ENHANCEMENT OF MONOCLONAL SCFV ANTIBODY AGAINST VENEZUELAN EQUINE ENCEPHALITIS VIRUS (VEE)

The application claims the benefit of provisional applications 60/275,103 and 60/341,843, filed on Mar. 12, 2001 and Dec. 21, 2001 respectively.

FIELD OF INVENTION

This invention relates to the cloning, expression, sequencing, mutagenesis and functional enhancement of reactivity of recombinant monoclonal single-chain variable fragment (ScFv) antibodies against Venezuelan equine encephalitis (VEE) virus antigens.

BACKGROUND OF THE INVENTION

List of Prior Art Literatures

Reference Formatting is Not Consistent

1. Johnston, R. E, Peters, C. J., "Alphaviruses", Fields, B. N., Knipe, D. M., Howley, P. M. et al. (Eds), FieldsVirology, third edition, Lippincott B Raven, Philadelphia, 1996, pp. 843-898.
2. Roehrig, J. T., et al. "Use of a new synthetic peptide derived monoclonal antibody to differentiate between vaccine and wild type Venezuelan equine encephalomyelitis viruses", J. Clinical Microbiol.,29, 3, pp.630-631, 1991.

Insert Other Authors

3. Schlesinger, S. and Schlesinger, M. J., "Togaviridae: The viruses and their replication", Fields, B. N., Knipe, D. M., Howley, P. M. et al.(Eds), Fields Virology, third edition, Lippincott B Raven, Philadelphia, 1996, pp. 825–841.
4. Anthony, R. P., Brown, D. T., "Protein-protein interaction in an alphavirus membrane", J. Virol., 65, pp. 1187–1194, 1991.
5. France, J. K., Wyrick, B. C., and Trent, D. W., "Biochemical and antigenic comparisons of the envelope glycoproteins of Venezuelan equine encephalomyelitis virus strains", J. Gen. Virol., 44, pp. 725–740, 1979.
6. Kohler, G., and Milstein, C., "Continuos culture of fused cells secreting antibody of predefined specificity", Nature, 256, pp.495–497, 1975.
7. Roehrig, J. T., and Mathews, J. H., "The neutralization site on the E2 glycoprotein of Venezuelan equine encephalomyelitis (TC-83) virus is composed of multiple conformationally stable epitopes", Virology, 142, pp. 347–356, 1985.
8. Bird, R. E., Hardman, K. D., Jacobson, J. W., Johnson, S., Kaufman, B. M., Lee, S. M., Lee, T., Pope, S. H., Riordan, G. S., and Whitlow, M., "Single chain antigen-binding proteins.", Science, 242, pp. 423–426, 1988.
9. Bird, R. E., and Webb-Walker, B., "Single chain antibody variable regions.", Trends Biotechnol., 9, pp. 132–137, 1991.
10. Better, M., and Horwitz, A. H., "Expression of engineered antibodies and antibody fragments in microorganisms.", Methods Enzymol., 178, 466–496, 1989.
11. Alvi A Z, Stadnyk L L, Nagata L P, Fulton R E, and Suresh M R: Development of second generation monoclonal functional single chain variable fragment (ScFv) antibodies against Venezuelan equine encephalitis virus (VEE): Cloning, Expression, Sequencing and functional analysis of two ScFv antibodies. Defence Research Establishment Suffield Report TR1999-033, 1999.
12. Sambrook J, Fritsch E F, and Maniatis T: Molecular Cloning, A Laboratory Manual, 2nd edition. Cold Spring Harbor Laboratory Press, Cold Spring Harbor, 1989.
13. Alvi A Z: Re-engineering of single chain variable fragment (ScFv) antibody. Final report for personal services contract #W7702-P059 to AFAM Alvi researchers and consultants. Submitted December 1999 to Defence Research Establishment Suffield.
14. Brewer J M, Pesce A J, and Ashworth R B (Eds): "Appendices", Experimental Techniques in Biochemistry, Prentice-Hall iinc, New Jersey, 1974, pp 328.
15. Kabat E A, Wu T T, Perry H M, Gottesman K S, and Foeller C: "Sequences of proteins of immunological interest", $5^{th}$ ed. U.S. Department of Health and Human services. Public Health Service, National Institutes of Health. Bathedsa, Md., 1991.
16. Kinney R M, Tsuchiya K R, Sneider J M, and Trent D W: "Molecular evidence for the origin of the widespread Venezuelan equine encephalitis epizootic of 1969–1972". J Gen Virol 1992; 73:3301–3305.
17. Weaver, S C, Salas R, Rico-Hesse R, Ludwig G V, Oberste M S, and Boshell J: "Re-emergence of epidemic Venezuelan equine encephalomyelitis in South America. VEE study group". Lancet 1996; 348: 436–440.
18. Roehrig J T, Day J W, and Kinney R M: "Antigenic analysis of the surface glycoproteins of a Venezuelan equine encephalomyelitis virus (TC-83) using monoclonal antibodies". Virology 1982; 118:269–278.
19. Hamilton R G: "Monoclonal antibodies in the diagnosis and treatment of human diseases". A Biol Clin 1989; 47:575–581.
20. Waldmann T: "Monoclonal antibodies in diagnosis and therapy". Science 1991; 252:1657–1662.
21. Ward S E, Gussow D, Griffiths A D, Jones P T, and Winter G: "Binding activities of a repertoire of single immunoglobulin variable domains secreted from *Escherichia coli*". Nature 1989; 341:544–546.
22. Sastry L, Alting-Mees M, Huse W D, Short J M, Sorge J A, Hay B N, Janda K D, Benkovic S J, and Lerner R A: "Cloning of the immunological repertoire in *Escherichia coli* for generation of monoclonal catalytic antibodies: Construction of a heavy chain variable region-specific cDNA library". Proc Natl Acad Sci USA 1989; 86:5728–5732.
23. Better M, Chang C P, Robinson R R, and Horwitz A H: "*Escherichia coli* secretion of an active chimeric antibody fragment". Science 1988; 240:1041–1043.
24. Skerra A and Pluckthun A: "Assembly of a functional immunoglobulin Fv fragment in *Escherichia col"i*. Science 1988; 240:1038–1041.
25. Alvi A. Z, Stadnyk L L, Nagata L P, Fulton R E, Bader D E, Roehrig J T, and Suresh M R: "Development of a functional monoclonal single-chain variable fragment antibody against Venezuelan equine encephalitis virus". Hybridoma 1999; 18:413 B 21.
26. Shibata Y, Kurihara K, Takiguchi H, and Abiko Y: "Construction of a functional single-chain variable fragment antibody against hemagglutinin from *Porphymonas gingivalis*". Infection and Immunity 1998; 66:2207–2212.
27. Ward E S: "Antibody Engineering using *Escherichia coli* as Host". Advances in Pharmacol 1993; 24:1–20.

The alphavirus family comprises of a large number of viruses that are closely related in their molecular structure but cause a variety of different diseases in humans and other animals [1]. Some alphaviruses, upon infection, enter the central nervous system (CNS) and lead to encephalitis. A New World Alpha virus of particular importance in this regard is Venezuelan equine encephalitis (VEE) virus. VEE virus infections mainly target the CNS and lymphoid tissues causing severe encephalitis in equines and systemic febrile infection with occasional encephalitis in humans. VEE virus is highly infectious by aerosol inhalation for humans [1].

Serologically the VEE complex of viruses can be subdivided into six subtypes (I–VI), with subtype I exhibiting five variants ($I_{AB}$, $I_C$, $I_D$, $I_E$, $I_F$) [1]. VEE epizootics are associated with members of subtypes $I_{AB}$ or $I_C$. The other subtype I variants ($I_D$, $I_E$ and $I_F$) and subtypes II–VI have been associated with enzootic VEE transmission [2].

The molecular structure of the VEE virion consists of a plus sense RNA genome encapsulated in an enveloped icosahedral nucleocapsid [3]. The envelope contains two important structural glycoproteins (gp), $E_2$ (56 KDa) and $E_1$ (50 KDa) [4]. The viral neutralization sites reside in the $E_2$ envelope protein [5]. Thus the $E_2$ protein of VEE is an important target for immunodetection/protection studies.

Hybridoma technology [6] made it possible to generate monoclonal antibodies (Mab) directed against viruses. The disadvantages of using monoclonal antibodies (Mabs) as immunodiagnostic or immunotherapeutic reagents are known. The cost of large-scale production of Mabs is excessive. The potential for genetic variations introduced during repeated cycles of cell growth make Mabs difficult to handle and potentially unreliable. In addition, antigenicity of the complete antibody molecule, when administered as therapeutic reagent, is associated with "serum sickness" in recipients. Furthermore, due to the large size of the whole antibody molecule, there is low penetrability of administered antibody into target tissues. These features make the complete antibody molecule unattractive for use as therapeutic reagent [19, 20].

However, with the development of recombinant antibody technology, where functional antibody fragments can be produced in bacteria, the application of antibodies as immunodiagnostic and/or immunotherapeutic reagents has become more feasible [21, 22, 23, 24].

To develop a monoclonal recombinant antibody from 1A4A-1 Mab, the inventors chose the Recombinant Phage Antibody System (RPAS). Briefly, in RPAS technology, the Variable heavy ($V_H$) and Variable light chain ($V_L$) domains of an antibody are cloned and covalently joined by a polypeptide linker in bacterial expression vectors generating single chain Variable fragment (ScFv) antibodies [8, 9, 10]. This results in expression in bacteria of the antigenic recognition domain of an antibody as a single chain, which can fold itself into a functional molecule. The attractiveness of this system is in the relative ease with which huge quantities of functionally active molecules can be obtained in a very short time. Since these ScFv lack the constant region of the antibody molecule, they have very low antigenicity. The low antigenicity of ScFv, coupled with their small size (~30 KDa) and hence the ease with which they can penetrate tissues, makes these molecules attractive alternatives to whole antibody molecules as therapeutic materials.

Roehrig et al. [7] generated Mab directed against VEE viruses. Using these Mab, the antigenic structure of the envelope glycoprotein $E_2$ of VEE virus was analyzed. Protection studies using anti-$E_2$ VEE virus Mab revealed a critical neutralization epitope ($E_2^c$). One of the Mab that recognized this neutralization epitope ($E_2^c$) was 1A4A-1. Mab 1A4A-1 not only recognizes VEE virus serological subtypes $I_A$–$I_D$ and $II_{EVE}$ in enzyme-linked immunosorbant assay (ELISA) but also can neutralize all of these subtypes [7], making it a very good candidate for development of second generation antibody with both diagnostic and immunotherapeutic application potential.

SUMMARY OF THE INVENTION

The present invention is directed to the cloning, expression, sequencing, mutagensis, and functional enhancement and of ScFv from hybridoma cell line 1A4A1.

The initial results of generating a recombinant 1A4A-1 ScFv antibody are described elsewhere [11]. Briefly, 1A4A-1 Mab was cloned as a ScFv antibody at Defence Research Establishment Suffield (DRES). The functional analysis of the 1A4A-1 ScFv (A116) by ELISA and western blotting revealed low reactivity to VEE whole virus antigen. Sequence analysis of A116 revealed three base deletions in the 5 prime end of the A116 $V_L$ gene. At the protein level, these mutations resided in the framework-1 region of $V_L$ of A116. The three individual base deletions introduced a localized frame shift in the first 20 amino acids of the conserved framework-1 region of $V_L$ of A116, resulting in a partially functional protein [11].

Framework-1 region of the light chain is highly conserved in antibody molecules. It adopts an anti-parallel beta pleated sheet conformation. β-strands A and B of the antibody light chain stabilize each other through hydrogen bonding and ultimately place complementarity determining region (CDR) L1 in proper context in relation to the other two CDRs for antigen interaction. Since the frame shift in $V_L$ of A116 occurred in a region that is conserved in antibody molecules, it is possible that the frame-shift affected the overall conformation of the antibody molecule, thus rendering it partially inactive. A repair strategy was conceived whereby the framework-1 region would be restored to consensus amino acid sequence, and such repaired clones could be analysed for restored reactivity to VEE whole virus antigen. In this invention, the inventors describe the successful isolation of MA116 clones with enhanced reactivity to VEE whole virus antigen and discuss the molecular changes that restored the full functionality of original A116 ScFv protein.

Through repairing the genetic mutation of the ScFv antibody gene, the present invention provides enhanced reactivity of the cloned ScFv antibody with homologous VEE antigen.

DETAILED DESCRIPTION OF THE INVENTION

Antibody Deposit Information

The various strains of antibodies developed in the present invention were deposited at the Bureau of Microbiology, Health Canada, at 1015 Arlington Street, Winnipeg, Manitoba, Canada, R3E 3R2. The deposit details are as follows:

Strain Accession Number

MA116-4 191103-02

MA116-6 191103-03

MA116-14 191103-04

MA116-15 191103-05

MA116-16 191103-06

Part I. Cloning Expression, Sequencing and Functional Analysis of ScFv from Hybridoma 1A4A1 Materials and Methods The Recombinant Phage Antibody System (RPAS), consisting of mouse ScFv module, expression module, and detection module, mRNA Quickprep™ kit, and anti-E Tag antibody labelled with horseradish peroxidase (HRP), was purchased from Amersham Pharmacia Biotech (Baie d'Urfé, QC). Taq polymerase used in polymerase chain reaction (PCR) was from Boehringer Mannheim (Laval, QC). Restriction enzymes were purchased from Gibco/BRL (Burlington, ON), Amersham Pharmacia Biotech, or New England Biolabs (Beverly, Mass.). Unless otherwise specified, chemical reagents were purchased from Sigma chemical company (St. Louis, Mo.) and tissue culture reagents were purchased from Gibco/BRL. Where possible, high grade reagents, nuclease-free water (Promega Inc., Madison, Wis.), siliconized microfuge tubes, pre-sterilized solutions, and disposable labware were used. Standard methods were used for the manipulation and cloning of cDNAs [12].

Cobalt-irradiated VEE strain TC83 was a gift from Dr. Jonathan Smith, U.S. Army Medical Research Institute of Infectious Diseases, Frederick, Md.

Growth and Maintenance of Hybridoma Cell Lines

VEE hybridoma clone 1A4A-1 was kindly provided by Dr. J. T. Roehrig, Division of Vector-borne Infectious Diseases, Centers for Disease Control and Prevention, Fort Collins, Colo. The hybridoma cells were grown and maintained in RPMI 1640 medium, supplemented with 10% heat-inactivated fetal bovine serum (Hyclone Laboratories, Logan, Utah), 2 mM L-glutamine, 1 mM sodium pyruvate, antibiotic/antimycotic supplement (100 units/mL penicillin G, 100 $\mu$g/mL streptomycin, and 25 $\mu$g/mL amphotericin B), 1× Vitamins solution, and 100 $\mu$M non-essential amino acids. The cells were maintained at a density of ~1×10$^5$/mL.

Construction of ScFv Antibody

Figure 1:
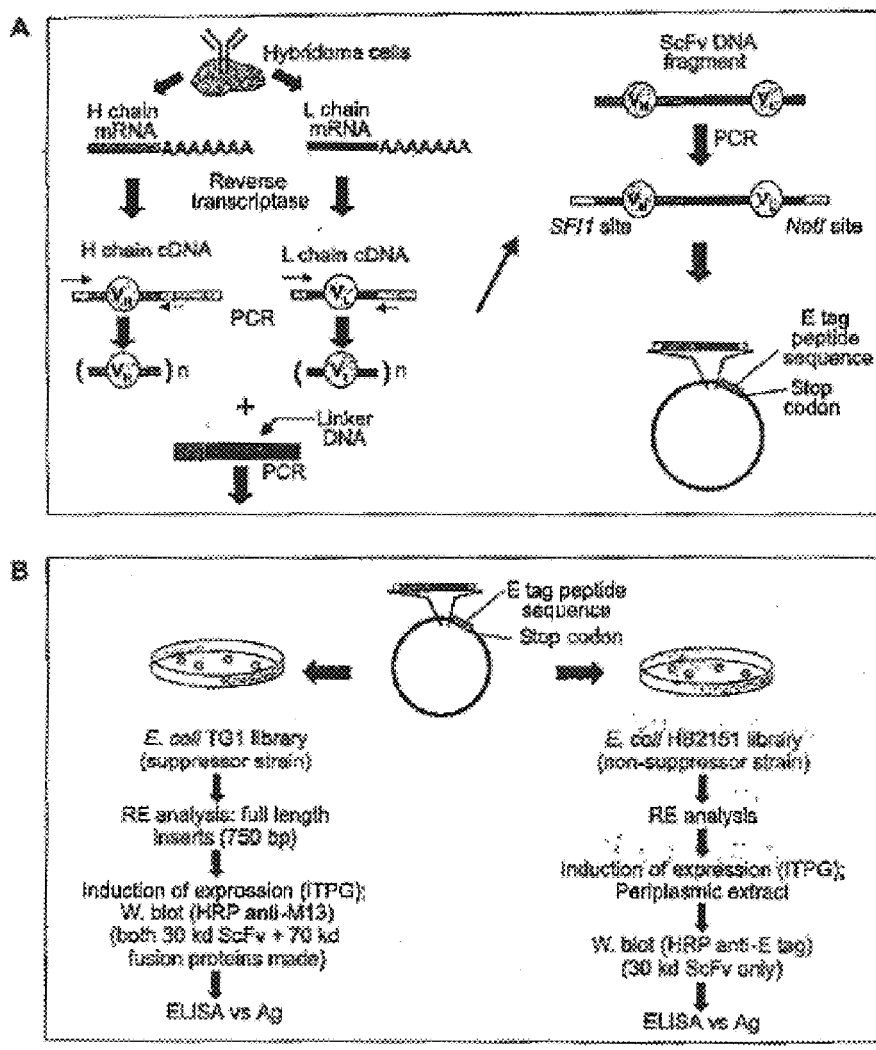
FIG. 1 is a schematic representation of steps in development of recombinant ScFv antibodies: A. Cloning and PCR; B. Expression and analysis.

A scheme representing the procedure adopted for cDNA cloning and construction of recombinant ScFv antibody is shown in FIG. 1 and described elsewhere (25). Messenger RNA was isolated from 1×10$^7$ hybridoma cells by use of a mRNA Quickprep™ kit (Amersham Pharmacia Biotech), in accordance with the manufacturer's recommended protocol. The final yield of mRNA was 8 $\mu$g. Two $\mu$g of mRNA was used as template for the reverse transcriptase reactions for each $V_H$ and $V_L$ chain. First strand cDNAs were synthesized by using primed, first strand reaction mixtures. The cDNAs coding for the respective $V_H$ and $V_L$ regions were then amplified by PCR by use of a set of primers included in the mouse ScFv module of the RPAS. PCR amplification was carried out for 30 cycles (94° C. for 1 min; 55° C. for 2 min; 72° C. for 2 min). Amplified DNAs of $V_H$ (~340–350 bp) and $V_L$ (~325 bp) were purified from incomplete products and primers by agarose gel electrophoresis. The purified $V_H$ and $V_L$ cDNAs (50 ng of each) were then mixed with linker DNA fragment. Assembly PCR was carried out for seven cycles (94° C. for 1 min; 63° C. for 4 min), thus connecting the two cDNAs in the correct reading frame. The assembled fragments were then amplified using primers with a Sfi I restriction site at the 5' end and a Not I site at the 3' end, to facilitate the cloning of the PCR products into the phagemid pCANTAB 5 E vector (Amersham Pharmacia Biotech). Phagemid pCANTAB 5 E is designed in such a way that the ScFv fragment can be cloned downstream to the leader peptide of the M13 gene 3 but upstream to the E Tag peptide, followed by an amber translational stop codon and the main body of the remaining M13 gene 3. The ligation mixture for the recombinant ScFv antibody was transformed into E. coli TG-1 competent cells (Amersham Pharmacia Biotech), an amber stop codon suppresser strain, and the transformed cells were subsequently plated on Luria Bertani (LB) agar plates containing 2% glucose and 100 $\mu$g/mL ampicillin. The plates were incubated overnight at 30° C.

Screening of ScFv Clones for Expression by Western Blotting

Individual phagemid clones of 1A4A1 ScFv recombinant antibody were picked and grown overnight in LB broth containing 2% glucose and 100 $\mu$g/mL ampicillin. Fresh 1.5 mL cultures were prepared the following morning at a starting $A_{600nm}$ of 0.05 and grown at 30° C. with shaking to a density of 0.5. Cells were then pelleted by centrifugation and resuspended in 1.5 mL fresh LB broth containing 100 $\mu$g/mL ampicillin and 3 mM iso-propyl β-D-thiogalactoside (IPTG). Subsequently, the cells were grown at 37° C. to an $A_{600nm}$ of 1.5 (~2 hours), pelleted again, resuspended in 0.6 mL of phosphate buffered saline (PBS), pH 7.5, and lysed by boiling. The boiled lysates were microfuged to remove cellular debris and the supernatants were frozen at −70° C. Three to six $\mu$L of each of the lysates were analyzed by sodium dodecyl sulfate-polyacrylamide gel electrophoresis (SDS-PAGE) on 12% gels. The separated proteins were transferred to Immobilon™-P membranes (Millipore Corp., Bedford, Mass.) by use of Towbin buffer (25 mM Tris/HCl, pH 8.3, 192 mM glycine, and 20% methanol). Membranes were blocked for one hour with blocking buffer (PBS containing 3% non-fat skim milk). HRP-labelled anti-E Tag antibody, diluted 1:2000 in blocking buffer, was then added and the membranes incubated in this solution for a period of 45–60 minutes. Specific binding to expressed ScFv was detected by use of an enhanced chemiluminescence (ECL) kit purchased from Amersham Pharmacia Biotech. For all washing steps, PBS containing 0.1% Tween-20 was used.

Expression of Soluble ScFv Antibody Molecules

DNA clone 1A4A1-16 was transformed into *E. coli* HB2151 cells (Amersham Pharmacia Biotech), an amber stop codon non-suppresser strain. The resulting transformants were referred to as A116. As described above for TG-1 cells, transformed HB2151 clones were grown in LB broth containing 2% glucose and 100 μg/mL ampicillin, were induced with IPTG, lysed by boiling, and the lysates submitted to SDS-PAGE and Western blot analysis.

Preparation of Periplasmic Extracts

Periplasmic extracts were made according to the protocol provided by Pharmacia Biotech, with the following variations. Overnight cultures were grown at 30° C. with shaking in 3 mL LB broth containing 2% glucose and 100 μg/mL ampicillin. Fresh 50 mL LB broth cultures, containing 100 μg/mL ampicillin, were prepared the following morning at a starting $A_{600nm}$ of 0.025. When the cultures had reached an $A_{600nm}$ Of 0.1(~1 hour), they were induced with 2 mM IPTG. The induced cultures were grown at 30° C. until they reached an $A_{600nm}$ of 0.5 (~2 hours). The cells were then harvested by centrifugation at 1500×g for 10 minutes and the pellet gently resuspended in 20 mL of ice cold 1× periplasmic extraction buffer (0.2 M Tris/HCl, 0.5 mM EDTA, and 0.5 M sucrose, pH 8.0) per liter of cell culture. Thirty-three mL of 0.2× periplasmic extraction buffer was added per liter of cell culture and the solution mixed. Cells were incubated on ice for 20 minutes with gentle agitation, then centrifuged at 1500×g for 10 minutes, and the supernatant collected and filtered through a 0.45μ filter (Millipore Corp.). Filtered supernatants were stored at −70° C.

ScFv Sequence Analysis

Plasmid DNA from 1A4A1-10, 1A4A1-12, 1A4A1-16, 1A4A1-17, 1A4A1-24, and 1A4A1-30 were used in double-stranded dideoxynucleotide sequencing, in both directions, using a pCANTAB 5 E sequencing primer set purchased from Amersham Pharmacia Biotech. Sequencing reactions were performed using a Big Dye™ Terminator Cycle Sequencing kit (Perkin Elmer Applied Biosystems, Mississauga, ON), as per the manufacturer's recommendations. The reaction products were purified from unincorporated dye molecules using Centri-Sep™ columns (Princeton Separations Inc., Adelphi, N.J.). The nucleotide sequence data was generated using an automated Prism™ 310 genetic analyzer system (Applied Biosystems, Foster City, Calif.). Results were analyzed on Lasergene DNA analysis software (DNA Star, Madison, Wis.). Protein search and analysis was performed on the PIR Release 58.0 (September 1998) and SWISS-PROT Release 36.0 (July 1998) databases, using Wisconsin package version 9.0 (Genetics Computer Group, Madison, Wis.). Subgrouping and family grouping were performed using the Kabat Database of Sequences of Proteins of Immunological Interest through Internet (February 1999 dataset) [15].

Enzyme-Linked Immunosorbant Assay

The enzyme-linked immunosorbant assay (ELISA) was carried out in 96-well Nunc Maxisorb™ flat-bottom plates (GIBCO/BRL, Bethesda, Md.). Inactivated VEE (strain TC-83) was used as antigen, at concentrations of 4 or 10 μg/mL. Wells were coated overnight at 4° C. with 100 μL VEE antigen prepared in 2× carbonate bicarbonate buffer, pH 9.6, containing 0.02% sodium azide. Plates were washed with PBS containing 0.05% Tween-20. Plates were blocked twice with blocking buffer (PBS containing 2% BSA and 0.05% Tween-20). Unless otherwise specified, primary antibody (ScFv lysate or periplasmic fraction) was diluted in antibody dilution buffer (PBS containing 2% BSA) and incubated for one hour at 37° C. HRP-labelled anti-E Tag antibody was used as indicator antibody and diluted 1:4000 or 1:6000 in antibody dilution buffer. Plates were developed with ABTS substrate solution (2,2'-azinobis [3-ethylbenzothiazoline-6-sulfonic acid] diammonium salt/ hydrogen peroxide 1:1 mixture) (Kirkegaard and Perry Laboratories, Gaithersburg, Md.). The plate blanks received blocking buffer and substrate only. Other appropriate controls were included in each assay.

Results

Cloning of ScFv Genes

Messenger RNA was isolated from hybridoma cell line 1A4A1 and cloned as ScFv by procedures outlined in FIG. 1. Distinct bands of ~340 bp for $V_H$ and ~325 bp for $V_L$ were detected by agarose gel electrophoresis after the first PCR amplification. The amount of $V_H$ product was estimated to be greater than the amount of $V_L$ product (data not shown). Gel purified cDNAs of $V_H$ and $V_L$ were assembled into their respective single gene 750 bp fragments and amplified by PCR. The gel purified 750 bp fragments, following digestion with the restriction enzymes SfiI and NotI, were ligated to phagemid vector pCANTAB 5 E and the ligation reaction transformed into *E. coli* TG-1 competent cells. Forty transformants of 1A4A1 ScFv were picked and grown individually for screening by "miniprep" DNA analysis. The remaining transformants were pooled and made into a 1A4A1 library.

Screening of Transformants for the Presence of Full Length ScFv Fragments

In order to screen for the presence of full length 750 bp ScFv inserts, "miniprep" DNA was prepared from the 40 individual transformants and restriction enzyme analysis was performed. From the 40 transformants, a total of six (1A4A1-10, 1A4A1-12, 1A4A1-16, 1A4A1-17, 1A4A1-24, and 1A4A1-30) were found to carry a full length 750 bp ScFv fragment (data not shown). These six transformants were selected for further analysis by western blotting, to evaluate for expression of the ScFv product.

Screening of Clones with Full Length Fragments for Expression in *E. coli* TG-1

Figure 2A:
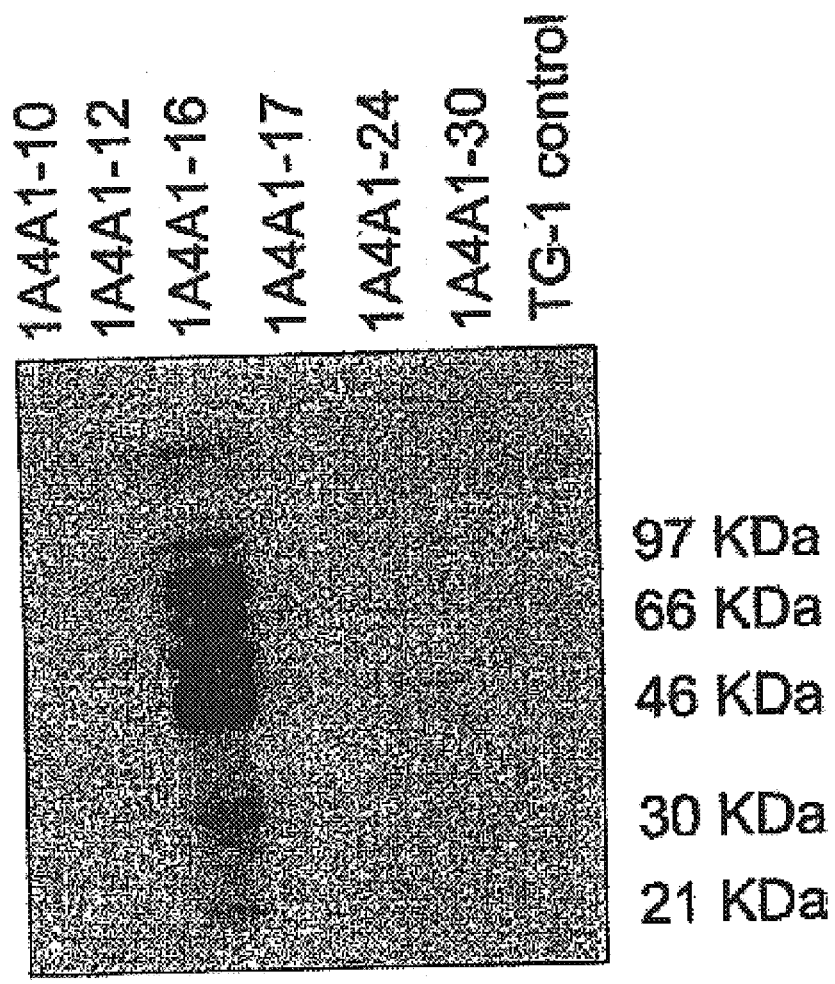
FIG. 2A shows Western blot of cell lystates from 1A4A1 clones exhibiting full length ScFv fragments, where 15 µl of lysate in a final volume of 25 µl was loaded per will on a 12% SDS-PAG gel, indicator antibody was HRP-labelled anti-E tag antibody. The position of molecular weight markers is indicated on the right hand side of the gel.

Following IPTG induction, cell lystates of the six TG-1 clones containing full length 1A4A1 ScFv were screened for expression of product by western blot analysis. *E. coli* strain TG-1 carries a suppressor transfer RNA for amber translational stop codons which allows suppression (readthrough) of the amber stop codon, present between the ScFv and gene 3 sequences of pCANTAB 5 E, at a frequency of about 20%. Therefore, both the ~70 KDa ScFv-gp3 fusion protein and the ~30 KDa ScFv soluble protein products were expected to be produced. FIG. 2A represents a western blot of cell lysates from the six 1A4A1 ScFv clones exhibiting full length ScFv fragments. Surprisingly, only clone 1A4A1-16 expressed protein products that were detected by anti-E Tag antibody. The other five 1A4A1 clones (1A4A1-10, 1A4A1-12, 1A4A1-17, 1A4A1-24, and 1A4A1-30) showed no expressed product. Since no background material was detected in the control TG-1 lysate by anti-E Tag antibody, it was deemed likely that the expression products seen in 1A4A1-16 lysate were from the ScFv full length fragment. As expected, both the soluble 30 KDa ScFv product and the ~70 KDa ScFv-gp3 fusion product were detected in the 1A4A1-16 lysate, as well as intermediate products that could have resulted either from degradation or incomplete synthesis.

Figure 2B:
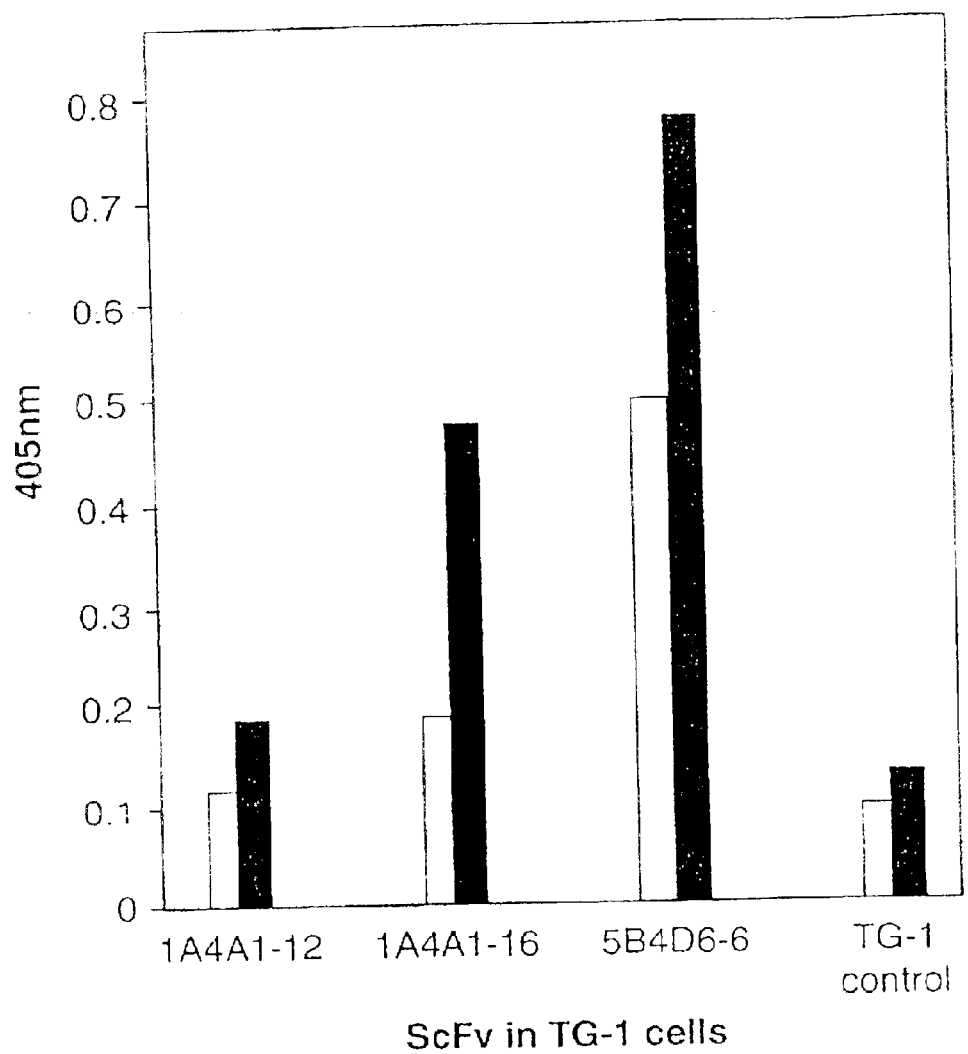
FIG. 2B shows screening of expression positive selected ScFv protein lysates from E. coli TG-1 cells for functional reactivity by ELISA, where wells were coated with 100 µl of inactivated VEE virus at a concentration of 4 µg/ml, and fifty µl of each test lysate was added per well. Indicator antibody was HRP-labeled anti-E tag antibody, diluted 1:4000 in antibody dilution buffer. Plates were read 30 minutes following addition of substrate solution. Data points are the mean of triplicate determinations.

Screening of 1A4A1-16ScFv Lysate from *E. coli* TG-1 for Recognition of VEE Antigen To assess the functionality of the expressed 1A4A1-16 ScFv products present in TG-1 lysates, ELISA was performed to test for reactivity with inactivated VEE antigen. TG-1 control cell lysates and lysates from 1A4A1-12 were included as negative controls, while 5B4D6 lysate, another VEE ScFv shown previously to react with VEE antigen [25], was used as positive control (FIG. 2B). Only 1A4A1-16 ScFv clone gave positive ELISA results, as indicated by retention of ScFv products in the presence of VEE antigen. Wells with VEE antigen specifically retained the expressed ScFv products at absorbance levels at least twice as high as that observed in wells without VEE antigen, indicating that 1A4A1-16 ScFv antibody was functionally active. It may also be observed from FIG. 2B that the 1A4A1-16 ScFv clone product, although functional, was less active than the 5B4D6 ScFv positive control lysate. The results of this ELISA complemented the expression results shown in FIG. 2A, with no activity demonstrated for the other 1A4A1 clones.

Expression of Functional Soluble ScFv Proteins in *E. coli* HB2151 Cells

To demonstrate the functionality of the soluble 30 KDa ScFv products when expressed in the absence of the ~70 KDa ScFv-gp3 fusion protein, 1A4A1-16 DNA was transformed into a non-suppressor background cell type, *E. coli* HB2151. To distinguish between TG-1 and HB2151 transformants, transformants obtained as a result of HB2151 transformations were referred to as A116, while TG-1 transformants were called 1A4A1-16.

Figure 3A:
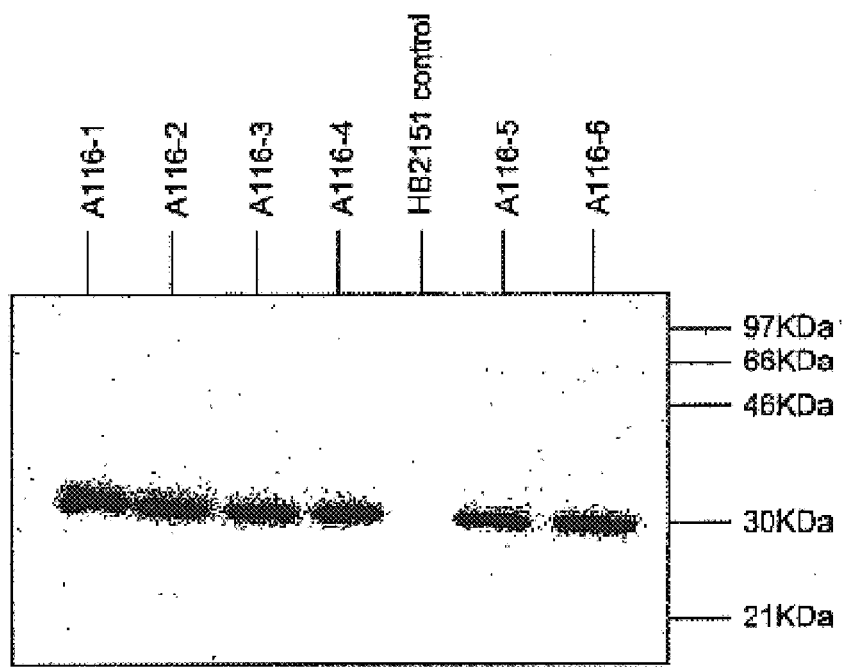
FIG. 3A shows screening of A116 ScFv protein in lysates of *E. coli* HB2151 cells for expression of soluble ScFv antibody by western blotting, where six μl of lysate in a final volume of 24 μl was loaded per well and electrophoresed on 12% SDS-PAGE gels. HRP-labeled anti-E tag antibody was used at 1:2000 dilution. The position of molecular weight markers is indicated on the right hand side of the gel.
Figure 3B:
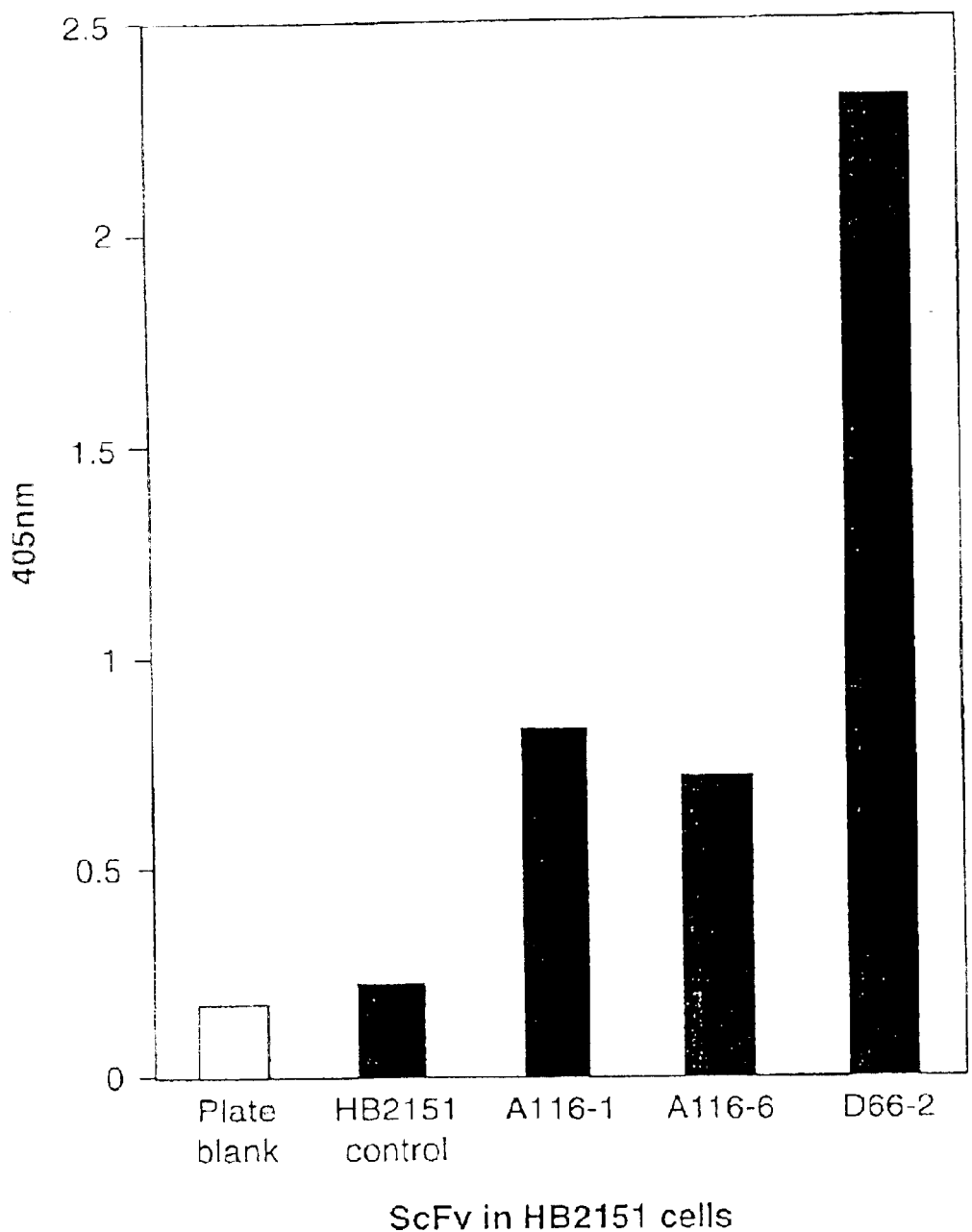
FIG. 3B shows screening of soluble ScFv protein in lysates from *E. coli* HB2151 cells for functional reactivity by ELISA, where wells coated with 100 μl of inactivated VEE virus at a concentration of 4 μg/ml, and fifty μl of each test lysate was added per well. Indicator antibody was HRP-labeled anti-E tag antibody, and diluted 1:4000 in antibody dilution buffer. Plates were read 30 minutes following addition of substrate solution. Data pints represent the mean of triplicate determinations. The position of molecular weight markers is indicated on the right hand side of the gel.

To establish that A116 clones expressed soluble 30 KDa ScFv protein, western blot analysis was performed on a number of different transformants. The cells were grown, induced with IPTG, and lysates made, as described above. The results of western blot analysis performed on the lysates of A116 transformants clearly showed the expression of 30 KDa soluble ScFv protein (FIG. 3A). Control *E. coli* HB2151 lysates did not show any detectable background. These results suggested that the A116 ScFv terminated correctly at the amber translational stop codon at the end of the E Tag. To show that the expressed soluble ScFv proteins in the A116 lysates were also functional, ELISA was performed with inactivated VEE, as described above for TG-1 lysates. HB2151 control lysates were included as negative controls (FIG. 3B). As observed in the ELISA of TG-1 lysates, A116 ScFv 30 KDa soluble proteins were functional in recognizing VEE antigen, with an observed approximate four-fold enhancement in absorbance over the HB2151 negative control lysate. Although functional, A116 ScFv 30 KDa soluble protein exhibited weaker interaction with the antigen when compared to an approximately equivalent concentration of D66 ScFv protein.

Analysis of Expressed ScFv Proteins from the Periplasm of *E. coli* HB2151 Cells It has been well documented that ScFv protein isolated from the periplasm is more active than ScFv protein present in the cytoplasm, because periplasmic protein is properly folded and in functional conformation. Conversely, most cytoplasmic ScFv protein is non-functional because it has not yet been properly folded. Activity assays reported in previous sections of this paper were performed using expressed ScFv extracted from whole cell lysates. It was hypothesized that ScFv A116 might be more sensitive to proper folding than was D66 and, for this reason, exhibited lower activity than D66.

Figure 4A:
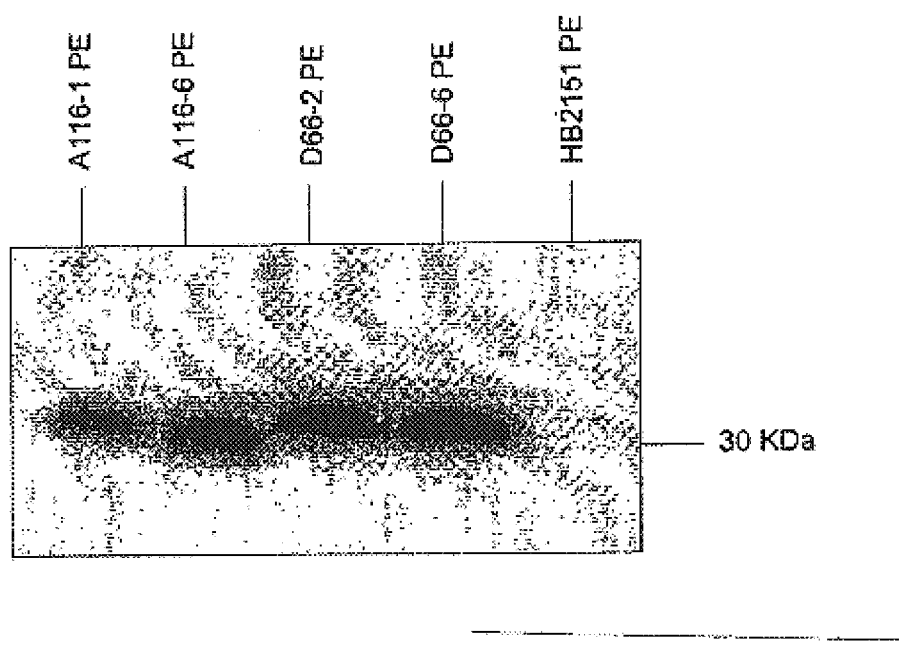
FIG. 4A shows Western blot of soluble A116 ScFv protein in periplasmic extract (PE) of *E. coli* HB2151 cells, where 15 μl of PE in a final volume of 25 μl was loaded per well and electrophoresed on a 12% SDS-PAGE gel. Indicator antibody was HRP-labeled anti-E tag antibody. The position o the 30 KDa molecular marker is indicated on the right hand side of the gel.
Figure 4B:
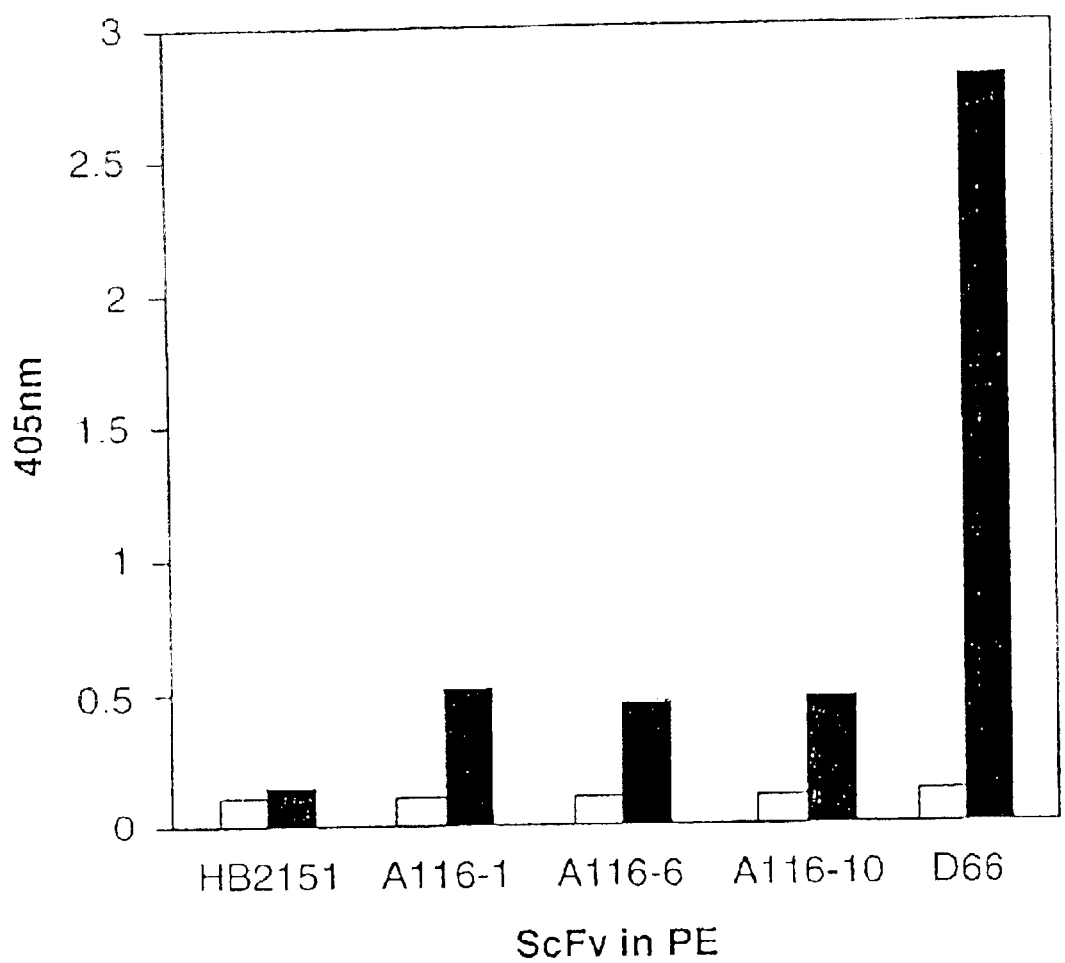
FIG. 4B shows functional analysis of A116 ScFv protein from periplasmic extract (PE) of *E. coli* HB2151 cells by ELISA, where wells were coated with 100 μl of inactivated VEE virus at a concentration of 10 μg/ml, and 30 μg of PE was diluted in antibody dilution buffer (PBS containing 0.1% Tween-20) to a final volume of 100 μl and added to the wells. Indicator antibody was HRP-labeled anti-E tag of purified fractions sere used. Al samples were tested in the presence and absence of bound VEE antigen in triplicate. Clear bars represent ScFv retention in the absence of VEE whole virus antigen. Solid bars represent retention of ScFv in the presence of VEE whole virus antigen. Gray bar is control PE in the presence of VEE antigen. Results represent 30 minute readings after the addition of substrate.

To determine if the functional reactivity of A116 ScFv could be enhanced by expression in the periplasm, A116 and D66 ScFv (positive control) proteins were extracted from periplasmic fractions and examined for expression by western blot and reactivity with VEE antigen by ELISA. FIG. 4A shows a Western blot demonstrating the presence of the 30 KDa expressed ScFv protein from both A116 and D66 periplasmic extracts analyzed. To test the functionality of the A116 ScFv expressed in the periplasm, an ELISA was performed (FIG. 4B). It was clear from the results of this ELISA that there was little difference in the activity of the A116 whether extracted from the periplasm (FIG. 4B) or from the whole cell lysate (FIG. 3B). This result suggested that the weak reactivity of A116 ScFv with VEE antigen was due to factors inherent in the primary structure of the protein rather than to issues relating to protein folding in the periplasm.

Nucleotide Sequence Analysis of 1A4A1 ScFv Clones

To investigate the reasons why the five full length 1A4A1 ScFv clones (1A4A1-10, 1A4A1-12, 1A4A1-17, 1A4A1-24, and 1A4A1-30) did not express ScFv products, their DNA was sequenced. In addition, DNA from clone 1A4A1-16 was sequenced, to identify the gene families for the $V_H$ and $V_L$ regions, as well as to elucidate potential mutations that might have contributed to its weak activity. It was also reasoned that, by knowing the nucleotide and deduced protein sequences, possible sequence defects could be identified and experiments could be designed to repair these defects and potentially re-engineer the antibody for improved activity.

Nucleotide sequences of the six 1A4A1 ScFv clones were generated, as described above, and amino acid sequences were deduced from the nucleotide sequence data generated (data not shown). The deduced amino acid sequences of the six 1A4A1 clones confirmed the expected protein structure, where $V_H$ and $V_L$ regions were connected by a linker region composed of $(Gly_4 Ser)^3$. It was further revealed that three of the five non-expressive 1A4A1 clones (1A4A1-10, 1A4A1-17, 1A4A1-24) had in-frame stop codons in the $V_H$, as well as in the $V_L$ genes and, therefore, could not express a protein product. The remaining two non-expressive clones (1A4A1-12 and 1A4A1-30), although free of any in-frame stop codons, were frame shifted, which resulted in an out-of-frame E-peptide sequence. Since anti-E Tag antibody was used for western blot detection of ScFv expression, this accounts for why the protein products expressed by these clones could not be detected.

Detailed analysis was performed on the nucleotide and amino acid sequences of clone 1A4A1-16 (A116). A comparison of the deduced amino acid sequences of the $V_H$ and $V_L$ regions of A116, as determined from the nucleotide sequence data, with other ScFv antibody amino acid sequences of murine origin available in the GCG protein database. Amino acid sequence analysis of A116 revealed what had been suspected i.e., that mutations had been introduced which resulted in a weakly active clone. The $V_H$ framework regions of A116 showed a high degree of homology with D66 and with the other murine ScFv used for sequence comparison. As expected, the sequence divergence was seen mainly in the three CDR regions (FIG. 5A). The C-terminal $V_L$ region also showed a high degree of homology in the framework regions and divergence in the three CDR regions, when compared to D66 or the published murine ScFv protein sequences (FIG. 5B). The protein sequence also diverged in the N-terminal first framework region of the $V_L$ chain of A116, located between the end of the linker and just before the beginning of the CDR1.

The nucleotide and amino acid sequences of the ScFv A116 were analyzed, using the Kabat Database of Sequences of Proteins of Immunological Interest (February 1999 Dataset), to determine the family grouping and subgrouping of the $V_H$ and the $V_L$ genes, respectively. To be included in a gene family, the database allows up to 34 base mismatches with existing sequences. The family grouping results for ScFv A116 $V_H$ were indeterminate, indicating that A116 $V_H$ is a unique sequence. This result could mean that either the $V_H$ gene belongs to a family that is under-represented in the database collection or, that the $V_H$ nucleotide sequence had mutated due to the accumulation of random single base changes during the PCR amplification steps. The $V_L$ nucleotide sequence was identified as belonging to the family XX, with 26 base mismatches. The amino acid sequences were analyzed for subgrouping and it was found that $V_H$ belongs to subgroup IA while $V_L$ belongs to subgroup V.

To determine the similarity of A116 ScFv $V_H$ and $V_L$ proteins with other murine antibodies, a similarity search of A116 sequence was performed using the GCG Word search program and two protein databases, PIR version 58.0 and SWISS-PROT version 36.0. Sequences showing a high degree of similarity were aligned for comparison. The ScFv A116 $V_H$, including the CDR regions, was compared and, on average, there was >75% similarity in the amino acids (FIG. 5A). This level of similarity is striking, considering that the CDR regions were included in the comparison. For the $V_L$ region, similarity was ~80% in the C-terminal proximal two-thirds portion of the $V_L$ protein (FIG. 5B).

FIG. 6 is a comparison of the nucleotide sequence of all six A116 clones in the region of the frame shift (Framework-1 of $V_L$). Deletions of three nucleotide bases at different positions in the N-terminal region of the $V_L$ of A116 were observed. Theoretically, if these deleted bases were to be introduced back into the nucleotide sequence and the amino acid sequence deduced, the frame-shifted region would be corrected to the consensus framework-1 region. This suggests that the deduced localized frame shift in the framework-1 region of $V_L$ is, indeed, genuine and was probably responsible for the observed weak binding of A116 ScFv antibody to the VEE antigen.

Discussion

ScFv antibodies offer several advantages over monoclonal antibodies generated by hybridoma technology, in that ScFv antibodies can be rapidly and economically produced, resulting in antibodies that are both functionally active and genetically stable (26. 27). In a previous publication, the present inventors reported the cloning and expression of D66 ScFv, a functionally active ScFv antibody produced from VEE hybridoma 5B4D6 (25). In this present study, the cloning and expression of another functionally active anti-VEE ScFv, A116, prepared from VEE hybridoma, 1A4A1, is disclosed.

VEE Mab 1A4A1, from which ScFv A116 was cloned in this study, has been previously well characterized by Roehrig et al. [18]. Parental Mab 1A4A1 is a neutralizing antibody, thus the cloning of this antibody as ScFv was of particular interest due to its potential usefulness as an immunotherapeutic reagent. In addition, the recombinant ScFv form of 1A4A1 MAb would be expected to be genetically more stable than its parental MAb. Furthermore, expression of recombinant ScFv in bacteria and purification therefrom could constitute a cost-effective alternative approach for the large-scale production of antibodies for ultimate use as VEE immunodetection reagents and/or immunotherapeutic reagents for the treatment of VEE-induced encephalitis.

Initial screening of the ScFv clones, to find full length 750 bp ScFv DNA, was performed by restriction enzyme analysis. Since the starting material for cloning had been a hybridoma cell line, our screening strategy relied on the fact that, theoretically, all clones were expected to contain the same ScFv, or fragments thereof. Thus a screening protocol was adopted that consisted of picking clones that contained 750 bp full length fragments rather than panning against antigen by phage display, a technique that is tedious and time-consuming. Clones containing full length ScFv DNA were then subsequently screened by western blot, to select for ScFv expression-positive clones. Initial screening of a total of 40 ScFv clones, by restriction digest analysis, revealed six clones with 750 bp inserts. Surprisingly, when probed with HRP-labeled anti-E Tag indictor antibody, only one of these clones, 1A4A1-16, showed expression of the desired size protein products. The E Tag peptide is expressed as an integral part of the soluble (30 KDa) ScFv, as well as the gp-3-fused (70 KDa) ScFv product, and ScFv molecules expressed in the correct frame can be immunodetected by using anti-E Tag antibody. By DNA sequencing, it was shown that three out of the six full length clones expressed ScFv products but, because of frame shifts, internal to the $V_H$ or the $V_L$ genes, the E-peptide was out-of-frame. Thus, the ScFv products expressed from clones 1A4A-12 and 1A4A1-30 with an out-of-frame E-peptide could not be detected in the western blot analysis. The observed increase in mutagenesis i.e., frame-shifts and introduction of non-sense codons seen in ScFv genes, can be explained by an inherent default in the cloning process. PCR reactions are known to introduce mutations due to the low fidelity of the proof-reading function of the thermo-polymerases used in the reaction. As both the $V_H$ and $V_L$ genes collectively undergo 60 cycles of PCR amplifications before cloning as ScFv genes, it is not surprising that increased mutagenesis was observed.

Functional analysis of the A116 ScFv antibodies by ELISA against VEE antigen showed that the A116 ScFv was functional in specifically recognizing VEE. The fact that A116 ScFv was not as reactive as D66 ScFv, a previously cloned anti-VEE ScFv, led the present inventors to further investigate the A116 clone from the perspective of its protein sequence. The A116 ScFv amino acid sequence was compared with that of D66 ScFv, as well as with ScFv sequences of murine origin. Amino acid sequence comparisons clearly indicated that the sequences were >75% homologous in all regions of both the $V_H$ and $V_L$ proteins, except in the CDR regions and the framework-1 region of the $V_L$ protein. The CDR regions are expected to be non-homologous, as they are responsible for antibody diversity and specificity. Framework regions of the antibody, on the other hand, are known to be highly conserved. However, framework-1 region of the $V_L$ protein of ScFv A116 was not conserved when compared to other murine $V_L$ amino acid sequences available in the database. Antibody specificity is attributed primarily to the $V_H$ protein, which confers the recognition of and crude binding to the target antigen. This initial interaction is fine-tuned by the $V_L$ protein, resulting in strong recognition and binding of the antigen. Additionally, framework regions of the antibody contribute to its function by putting the CDR regions in the proper configuration to interact optimally with the epitope on the target antigen. To explain the lower reactivity of A116 ScFv antibody compared to D66 ScFv, the present inventors propose that, because of a localized frame shift in the framework-1 region of the A116 $V_L$, the antibody was unable to assume a functional conformation that would allow optimal interaction with the epitope on VEE antigen. The lack of homology in the framework-1 region of A116 ScFv, supports this hypothesis. By comparing the nucleotide sequences of the six 1A4A1 ScFv clones, the three individual nucleotide deletions that could have caused the proposed localized frame shift were located. It is likely that, if the deleted nucleotides were to be added back to the A116 nucleotide sequence, in the proper context, the consensus framework-1 region amino acid sequence would be restored.

In summary, a recombinant ScFv antibody has been generated from a well-characterized MAb to VEE virus. This ScFv, designated A116, was shown to be minimally reactive with the target VEE antigen when compared to another VEE ScFv previously cloned by this laboratory. By investigation of the nucleotide and deduced amino acid sequences of the $V_H$ and $V_L$ chains of A116 ScFv, mutations were identified that could have accounted for its reduced reactivity with antigen.

Part II. Functional Enhancement of Reactivity of ScFv

Materials and Methods

Restriction enzymes and polynucleotide kinase were purchased from Amersham Pharmacia Biotech. PCR extra long kit was purchased from Perkin-Elmer/Applied Biosystems (Mississauga, ON). Unless otherwise specified, chemical reagents were purchased from Sigma Chemical Company (St. Louis, Mo.). Where possible, high-grade reagents, nuclease-free water (Promega Inc., Madison, Wis.), siliconized microfuge tubes, pre-sterilized solutions, and disposable labware were used. Standard methods were used for the isolation and manipulation of DNA [12].

Synthesis of Primers

Two primers were synthesized for this study. A116 forward primer was a 20 mer with a sense polarity and carried the 5 prime distal-most insertion of a "T" (denoted as third insertion). The sequence of forward primer synthesised was 5'caa-att-cgt-Tgt-cca-cat-ca 3'(with upper case T indicating the third base insertion). A116 reverse primer was a 30 mer with anti-sense polarity and carried the first two 5 prime proximal "T" insertions which would appear on the sense strand as "A" (denoted as first and second insertions). The sequence of reverse primer synthesised was 5' gag-acT-gag-tga-gct-cga-Tgt-ccg-atc-c 3' (with upper case T indicating the first and the second base insertions).

PCR-Based Site Directed Mutagenesis and Amplification of A116 DNA

Figure 7:
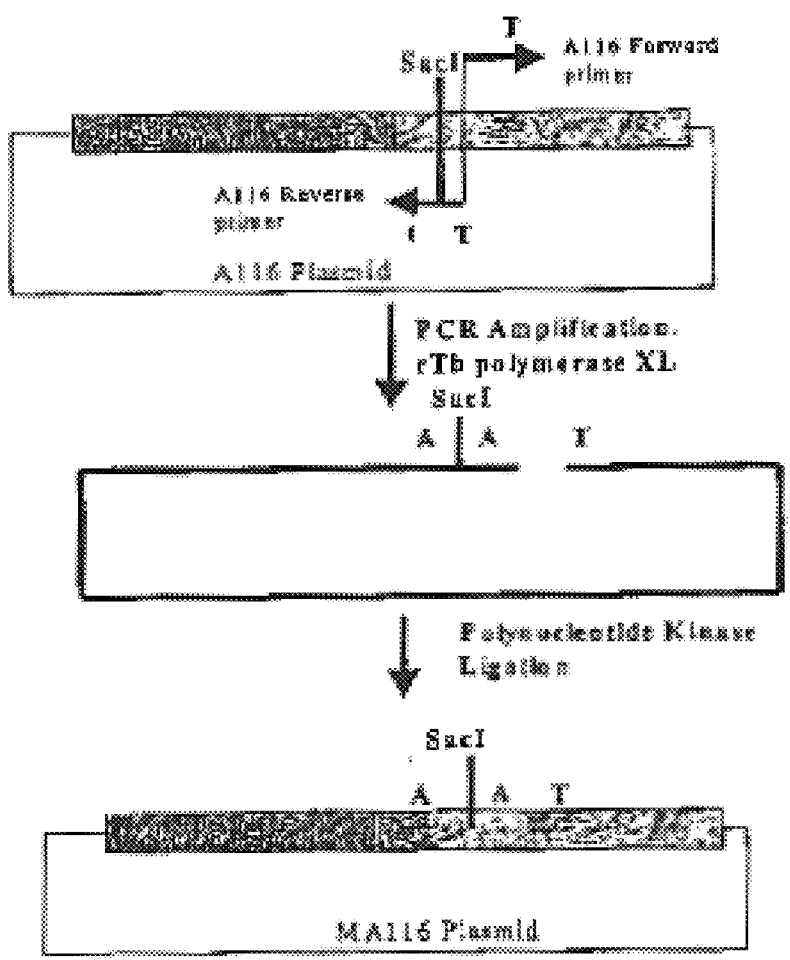
Figure 8:
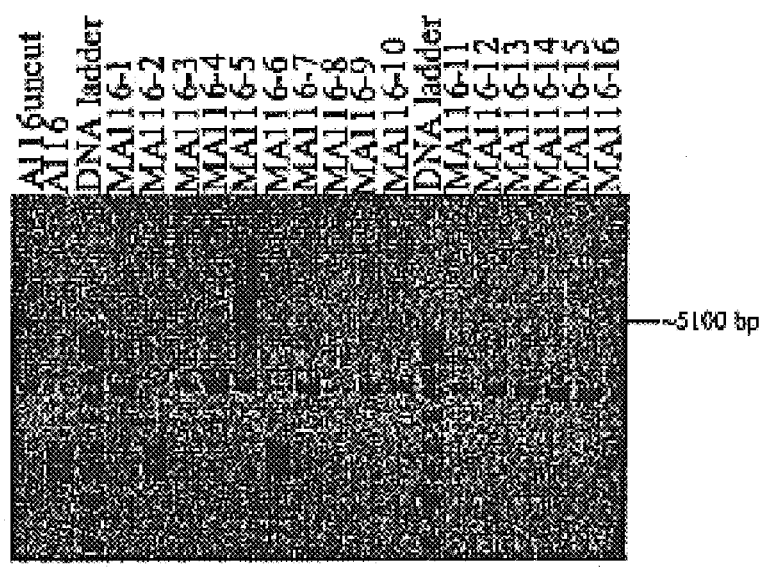

The strategy for PCR-based site directed mutagenesis and DNA amplification is outlined in FIG. 7. Two and 5 ng of A116 DNA were used in the PCR reactions. Final concentration of the primers in the reaction was 800 nM. The reaction conditions and other ingredients were as recommended by the manufacturer of GeneAMP$^R$ XL PCR kit (Perkin-Elmer/Applied Biosystems). Special polymerase was used for this particular PCR reaction. The enzyme rTth DNA polymerase, XL(Perkin-Elmer/Applied Biosystems) has been genetically modified to give better performance in PCR reactions where extra long DNA synthesis is required. Four units of this polymerase were added per reaction. The PCR reaction (denaturation at 94° C. for one minute, annealing at 56° C. for two minutes, extension at 72° C. for five minutes) was performed for 25 cycles. PCR reactions amplified a 5100 bp band, that was subsequently purified by standard DNA purification methods. The purified PCR-amplified DNA was subjected to reaction with polynucleotide kinase (Amersham Pharmacia Biotech), in accordance with the manufacturer's recommendations. The end phosphorylated PCR-amplified DNA was gel purified again and ligated, overnight at 15° C., with T4 DNA ligase (Amersham Pharmacia Biotech). The ligation reaction product was used to transform E. coli HB2151 competent cells, and the resulting transformation reaction was plated on Luria-Bertani (LB) agar containing 100 ug/mL ampicillin and incubated overnight at 37° C. The individual colonies that grew were treated as individual clones. Mini preparation of DNA was prepared from individual colonies after growth in LB broth media by standard protocols (12). The restriction digestions were performed according to standard protocols (12).

Preparation of Whole Cell Lysates of MA116 ScFv Clones

Individual re-engineered clones of A116 ScFv recombinant antibody were grown overnight in LB broth containing 2% glucose and 100 µg/mL ampicillin. Fresh 1.5 mL cultures were prepared the following morning at a starting $A_{600nm}$ of 0.05 and grown at 30° C. with shaking to a density of 0.5. Cells were then pelleted and resuspended in 1.5 mL fresh LB broth containing 100 µg/mL ampicillin and 3 mM iso-propyl β-D-thiogalactoside (IPTG). Subsequently, the cells were grown to an $A_{600nm}$ of 1.5 (~2 hours) at 37° C. and were pelleted again and resuspended in 0.6 mL of phosphate-buffered saline (PBS), pH 7.5, and lysed by boiling. The boiled lysates were microfuged to remove cellular debris and the supernatants were frozen at –70° C. Nine µL of each of the lysates were analyzed by sodium dodecyl sulfate-polyacrylamide gel electrophoresis (SDS-PAGE) on 10% gels followed by western blotting (see below).

Preparation of Periplasmic Extracts

Periplasmic extracts were made according to the manufacturer's protocol (Amersham Pharmacia Biotech, Baie d'Urfé, QC), with the following variations. Overnight cultures were grown at 30° C. with shaking in 30 mL LB broth containing 2% glucose and 100 µg/mL ampicillin. Two 1 Liter LB broth cultures containing 100 µg/mL ampicillin, were prepared in the morning at a starting $A_{600nm}$ of 0.05 and grown at 37° C. When the cultures had reached an $A_{600nm}$ of 0.25 (~2 hour), they were induced with 2 mM IPTG. The cultures were grown at 37° C. for three hours. The cells were harvested by centrifugation at 1500×g for 10 minutes. The pellet was gently resuspended in 20 mL of ice cold 1× periplasmic extraction buffer (0.2 M Tris/HCl, 0.5 mM EDTA, 0.5 M sucrose, pH 8.0) per liter of cell culture. Thirty-three mL of 0.2× periplasmic extraction buffer was added per liter of cell culture and the solution mixed. Cells were then incubated on ice for 30 minutes with gentle agitation, then centrifuged at 10,000×g for 10 minutes and the supernatant collected and filtered through a 0.45µ filter (Millipore Corp., Bedford, Mass.). Filtered supernatants were stored at –70° C.

Purification of MA116-15 ScFv from Periplasmic Extract

Purification of MA116-15 ScFv was carried out by use of a RPAS antibody purification kit from (Amersham Pharmacia Biotech), according to the manufacturer's recommendations, with the following variation. The periplasmic extract (100 mL) was passed through the anti-E tag affinity column at a much slower constant rate of ~1 mL per minute, by use of a peristaltic pump. Ten fractions (1 mL each) were collected at the elution step.

Analysis of ScFv Proteins by Coomassie Staining and Western Blot

Ten µL of each purified MA116-15 protein fraction was analyzed by SDS-PAGE on duplicate 10% gels. The separated proteins on one gel were stained by Coomassie brilliant blue R-250 stain [12]. The separated proteins on the second gel were transferred to Immobilon™-P membranes (Millipore Corp.) by use of Towbin buffer (25 mM Tris/HCl pH 8.3, 192 mM glycine, 20% methanol). Membranes were blocked for one hour with blocking buffer (PBS containing 3% non-fat skim milk). HRP-labeled anti-Etag antibody (Amersham Pharmacia Biotech), diluted 1:1000 in blocking buffer, was then added and the membranes incubated in this solution for a period of 60 minutes. Specific binding to expressed ScFv was detected by use of an enhanced chemiluminescence (ECL) kit purchased from Amersham Pharmacia Biotech. For all washing steps, PBS containing 0.1% Tween-20 was used.

Sequence Analysis of ScFv MA116 Re-engineered Clones

Purified plasmids of four MA116 clones (MA116-2, MA116-4, MA116-6, MA116-14, MA116-15, and MA116-16) were used in double-stranded dideoxynucleotide sequencing in both directions using a pCANTAB5E sequencing primer set purchased from Amersham Pharmacia Biotech. Sequencing reactions were performed using the Big Dye™ Terminator Cycle Sequencing kit (Perkin Elmer/Applied Biosystems), according to the manufacturer's recommendations. The reaction products were purified from unincorporated dye molecules using Centri-Sep™ columns (Princeton Separations Inc., Adelphi, N.J.). The nucleotide sequence data was generated using an automated Prism™ 310 genetic analyzer system (Perkin Elmer/Applied Biosystems). Results were analyzed on Lasergene DNA analysis software (DNA Star, Madison, Wis.).

VEE Virus

Gamma-irradiated, purified VEE virus, strain TC83, was a gift from the United States Army Medical Research Institute of Infectious Diseases (USAMRIID), Frederick, Md.

Enzyme-Linked Immunosorbant Assay

Enzyme linked immunosorbant assay (ELISA) was carried out in 96-well Nunc Maxisorb™ flat bottom plates (GIBCO/BRL, Bethesda, Md.). Inactivated whole VEE virus (strain TC-83) was used as antigen, at a concentration of 10 $\mu$g/mL. Wells were coated overnight at 4° C. with 100 $\mu$L VEE antigen prepared in 2× carbonate bicarbonate buffer, pH 9.6, containing 0.02% sodium azide. Plates were washed with PBS containing 0.05% Tween-20. Plates were blocked twice with blocking buffer (PBS containing 2% BSA and 0.05% Tween-20). Unless otherwise specified, primary antibody (ScFv lysate) was diluted in antibody dilution buffer (PBS containing 2% BSA and 0.1% Tween-20) and incubated for one hour at 37° C. HRP-labeled anti-E tag antibody (Amersham Pharmacia Biotech), diluted 1:6000 in antibody dilution buffer, was used for the detection of MA116 ScFv molecules. HRP-labeled anti-mouse antibody (Jackson ImmunoResearch Laboratories) (Bio/Can Scientific, Mississauga, ON), diluted 1:3000 in antibody dilution buffer, was used for the detection of MAb. Plates were developed with ABTS substrate solution (2,2'-Azinobis [3-ethylbenzothiazoline-6-sulfonic acid] diammonium salt/hydrogen peroxide, 1:1 mixture) (Kirkgaard and Perry Laboratories) (Canada Life Technologies, Burlington, ON). The plate blanks received blocking buffer and substrate only. Other appropriate controls were included in each assay.

Results

Following PCR-based site directed mutagenesis and amplification of the mutagenized A116 plasmid (MA116), a distinct linearized DNA band of ~5100 bp was detected by agarose gel electrophoresis (data not shown). The gel purified 5100 bp MA116 linear DNA was phosphorylated at the ends with polynucleotide kinase to make it ligation competent. The phosphorylated MA116 linear DNA was gel purified and ligated. This ligated MA116 circular DNA was then transformed into *E. coli* HB2151 competent cells. Approximately 70 transformants were obtained.

Screening of Transformants for the Loss of XhoI Restriction Enzyme Site

To screen MA116 transformants, 16 individual colonies were picked and mini-preparation DNA was isolated for XhoI restriction enzyme digestion analysis. A116 ScFv plasmid contains two XhoI restriction enzyme sites. One of these sites is present on the plasmid outside of the ScFv gene while the second XhoI site resides in the 5 prime end of VL gene. It was reasoned that incorporation of the first "A" into the A116 sequence would destroy the second XhoI site. Thus MA116 clones that gave linear 5100 bp DNA bands upon digestion with XhoI, would have incorporated at least one of the three intended insertions. From XhoI restriction enzyme digestion analysis of 16 MA116 transformants (FIG. 2), all except two showed a distinct 5100 bp linear DNA band, indicating that PCR site directed mutagenesis had been successful. The two MA116 clones (MA116-2, and MA116-6) showed digestion patterns which were identical to the wild type A116 un-mutagenized DNA (FIG. 8).

Screening of MA116 Clones for Expression and Function in *E.coli* HB2151 Cell Lysates Since *E. coli* HB2151 has a non-suppresser background, only the 30 KDa soluble ScFv product would be synthesized if the ScFv open reading frames (ORF) were free of amber stop codons.

To establish that MA116 clones expressed soluble 30 KDa ScFv protein, Western blot analysis was performed on a number of different transformants. The cells were grown, induced with IPTG, and lysates were prepared, as described above. Western blot performed on the lysates of selected MA116 clones showed the expression of 30 KDa soluble ScFv proteins for clones MA116-4, MA116-6, MA116-14, MA116-15, and MA116-16, while lysates of MA116 clones MA116-1, MA116-2, MA116-3, and MA116-8 were negative for protein expression (FIG. 9). Control *E. coli* HB2151 lysates did not show detectable background. These results strongly suggested that clones MA116-4, MA116-6, MA116-14, MA116-15, and MA116-16 were free of amber translational stop codons in their ORF.

Functional Confirmation of Five MA116 Clones by ELISA

Fresh whole cell lysates were made from the parental A116 clone and five MA116 clones (MA116-4, MA116-6, MA116-14, MA116-15, and MA116-16) and induced with 2 mM IPTG for expression of ScFv antibody. These lysates were then used to evaluate their relative reactivity to VEE antigen, in relation to parental A116, by ELISA. The ELISA reactivity of the ScFv was determined, in triplicate, in the presence and absence of VEE whole virus antigen, for each of the five MA116 re-engineered MA116 clones and parental A116 clone (FIG. 10). MA116-15 was the most reactive clone, being four times more active than the original A116 clone in recognizing VEE antigen. MA116-14 and MA116-16 also showed good reactivity, being two to two and one-half times more reactive than the original A116 clone. MA116-4 and MA116-6, although active, were less active than the parental A116 clone. All five MA116 clones showed specific retention, at least two and one-half-fold greater, in the presence of VEE antigen as compared to non-specific retention in the absence of VEE antigen.

Sequencing of MA116 Re-Engineered Clones

Sequencing of selected MA116 clones (MA116-4, MA116-6, MA116-14, MA116-15) was carried out to establish the incorporation of the three intended base insertions in the proper context of the re-engineered MA116 genes. Furthermore, sequencing was performed to rule out random mutations that might have accumulated in the PCR mutagenesis step. The nucleotide sequences of MA116 and A116 clones, as determined by sequencing, compared to the consensus sequence in the region of intended base insertions, is shown in FIG. 11. As deduced from FIG. 11, in clone MA116-15, all three bases were inserted at the pre-defined target positions, making the sequence of this re-engineered clone identical to that of the consensus sequence. MA116-4 also showed insertion of all three nucleotide bases at the intended positions but, there were accumulated additional mutations also noted i.e., deletion of A at nt 398 and insertion of T after nt 419. MA116-6 did not incorporate any intended changes, but additional mutations were observed. MA116-14 incorporated the expected insertions, similar to MA116-15, however, an additional insertion of a C occurred after nt 419, and a deletion at nt 433 frame-shifted the reading frame back to the MA116-15 reading frame. MA116-16 also incorporated the expected changes of MA116-15, but a point mutation at nt 46 (C replaced by a T) caused an amino acid change.

Figure 10:
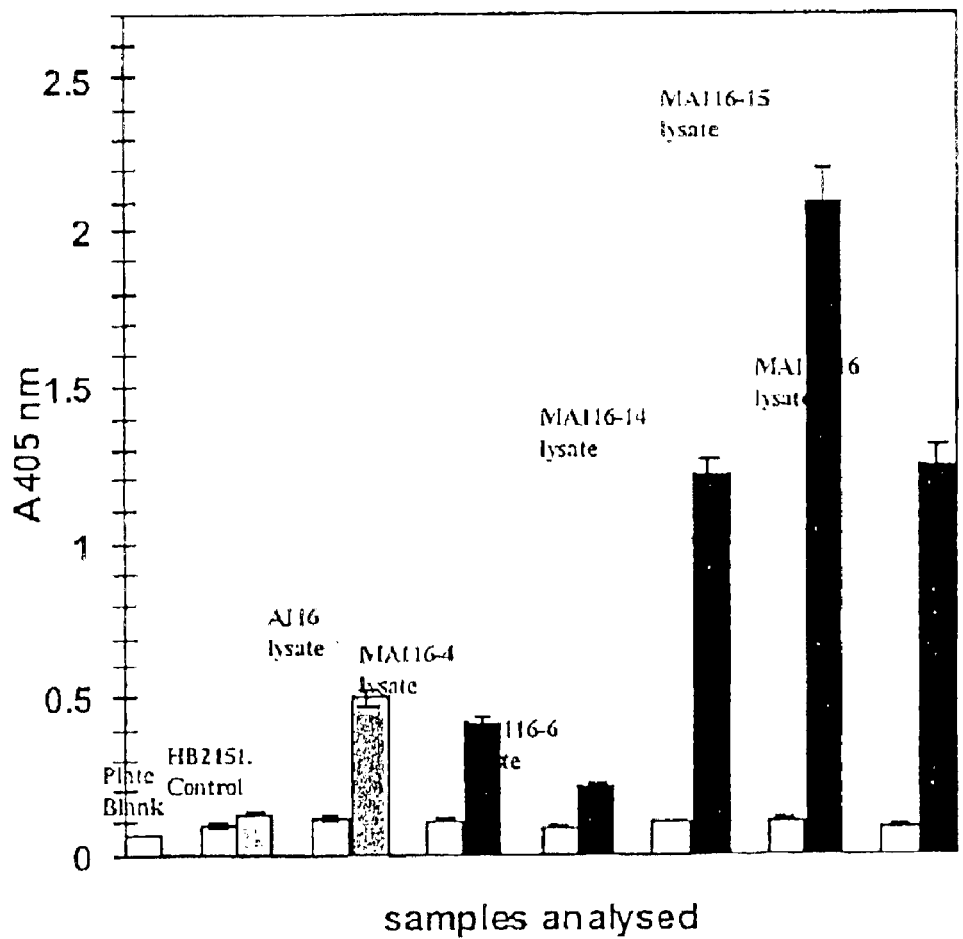

The results of the mutagenesis are best illustrated in the deduced amino acid sequence alignment performed using the Clustal W program of DNASTAR. As illustrated in FIG. 12, A116-16 has a major alteration in sequence in the Framework-1 region of the light chain (residues 134–142), when compared with the MA116 sequences. In addition, A116-16 contained additional difference at residues 77 and 79 of the heavy chain, and residue 226 of CDR-L3 were also noted. MA116-6 was identical to A116-16 in Framework-1, and had one addition change at residue 59 in CDR-H2. MA116-4 was changed from the MA116-15 from residues 133-140, as well as a conserved change at residue 213. MA116-14 contained a 4 amino acid change from MA116-15 in Framework-1 (residues 141–144), and a conserved change at residue 210. Lastly, MA116-16 was identical to MA116-15, except for a radical substitution at residue 16. Interestingly, the deduced amino acid changes follow the reactivity of the expressed protein in ELISA (FIG. 10). The most altered Frame-work 1 clones: A116-16, MA116-6 and MA116-4 (FIG. 12), showed the lowest reactivity. MA116-14 and MA116-16 demonstrated intermediate activity in recognition of VEE on ELISA (FIG. 10), one in Framework-1 (MA116-14) and one outside Framework -1 (MA116-16). The E-tag was identical for all 6 clones, and was not included for comparison in FIG. 12. As MA116-15 was the correctly repaired, showed no additional mutations from the MA116 consensus and demonstrated the highest activity, it was chosen for further evaluation.

Purification and Functional Analysis of Ppurified MA116-15 ScFv Antibody

MA116-15 was chosen for purification, based on this clone being the most active and the most molecularly "correct" of the MA116 clones. An anti-E tag affinity column (Amersham Pharmacia Biotech.) was used to purify MA116-15 ScFv antibody from the periplasmic extract of MA116-15 clone. To determine the level of purification and to estimate the protein concentration of the purified ScFv, the collected fractions were analyzed by SDS-PAGE (FIG. 11). For estimation of the protein concentration of purified MA116-15 ScFv, a known concentration (400 ng) of another purified ScFv, D66 (25) was also loaded on the gels. FIG. 13A represents a Coomassie stained gel. The D66 ScFv protein was detected on the gel at a molecular weight of approximately 32 Kda. Higher molecular weight bands were seen in all the lanes of Coomassie stained gel but fraction six of MA116-15 showed a faint band at a similar molecular weight to the D66 ScFv. FIG. 13B is a western blot of a gel, loaded identically to the Coomassie stained gel; the presence of MA116-15 ScFv in fractions six, seven and eight is visible. This western blot confirmed that the faint band seen in purified fraction six of MA116-15 ScFv (FIG. 13A) was, indeed, the purified MA116-15 single chain antibody. Fraction 6 appeared to be the most concentrated fraction of the MA116-15 ScFv protein, followed by fraction seven. Fraction eight is the least concentrated fraction of MA116-15 ScFv protein. In addition, from FIG. 13B, it was evident that the higher molecular weight bands, as seen in FIG. 13A, were not multimers of MA116-15 ScFv, as those bands were not recognized by the anti-E tag antibody.

Figure 13C:
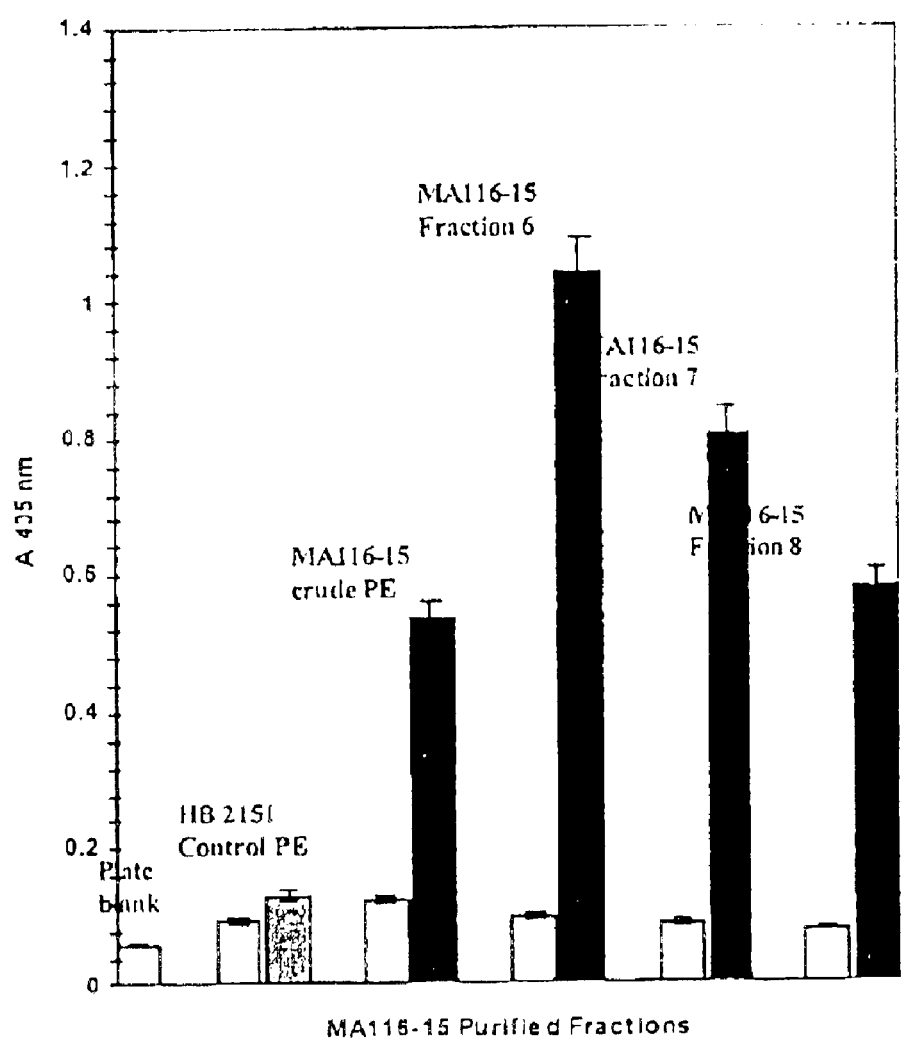

To further confirm that fractions six, seven and eight contained purified MA116-15 ScFv antibody and that this was, indeed, functional, ELISA was performed.Equal volumes of purified MA116-15 fractions six, seven, and eight were analysed by ELISA, in triplicate, in the presence and absence of VEE antigen., The ELISA results are depicted in FIG. 13C. ELISA results were consistent with the western blot data in FIG. 13B. The fractions most reactive with the VEE antigen by ELISA were, in order of decreasing magnitude, fraction six, followed by fractions 7 and 8. Similarly, by western blot analysis, fraction 6 was the most concentrated of the three ScFv fractions, followed by fraction seven; fraction 8 contained the least amount of purified MA116-15 protein.

Functional Comparison of Purified MA116-15 ScFv with the Pparent 1A4A-1 MAb

To compare the reactivity of the purified, functionally enhanced MA116-15 ScFv with the 1A4A-1 MAb in recognizing VEE whole virus antigen, an ELISA was performed. Since a functional comparison of the two species of antibodies was at issue, it was important that functionally equimolar quantities of the two proteins must be used in ELISA. Equimolar calculations were based on the fact that the ScFv molecule is approximately five times smaller than the monoclonal antibody molecule in terms of molecular weight. Thus, at a given concentration of protein, there would be five times more molecules of ScFv than Mab. Since there are two reactive sites on a Mab and only one reactive site on the ScFv molecule, the functional ratio of ScFv to Mab would be 1:2.5. Thus, for every given unit of concentration of MA116-15 ScFv by ELISA, the corresponding equimolar amount of 1A4A-1 Mab would be 2.5 times greater.

Figure 14:
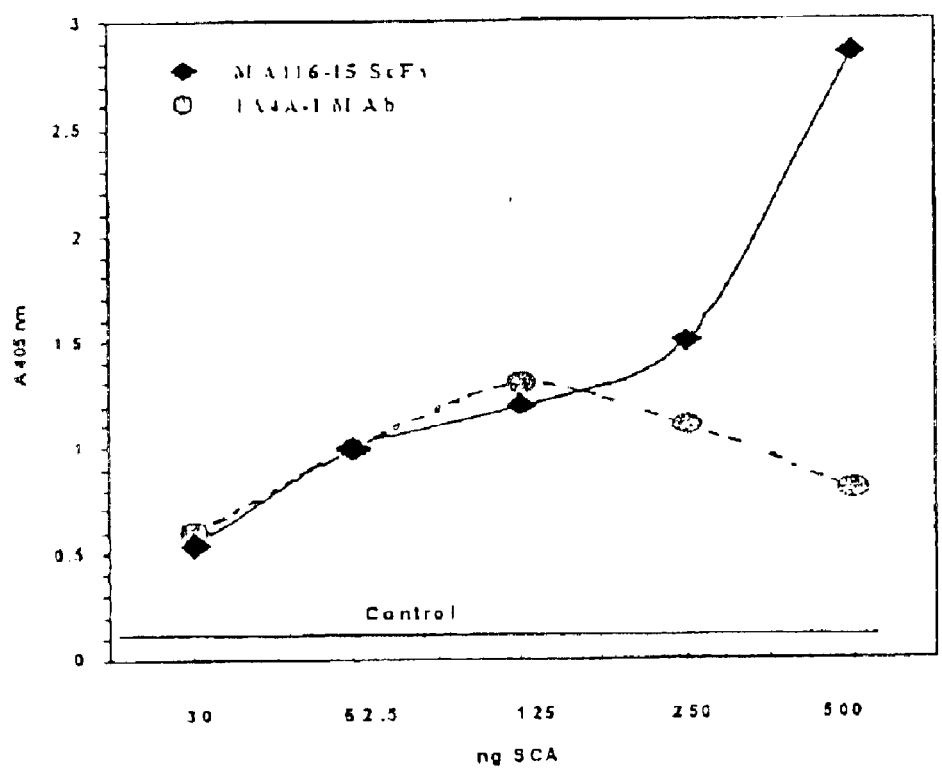
FIG. 14 shows functional comparison of purified MA116-15 (F6) ScFv and parent 1A4A-1 Mab at equi-molar concentration, according to an ELISA analysis performed by adding increasing equimolar amounts of the respective proteins. The X-axis represents the amount of ScFv added. The amount of MAb at each variable point is 2.5× higher (e.g. at 30 ng ScFv, the amount of MAb is 75 ng). VEE purified whole virus antigen was coated on the plate at 10 $\mu$g/ml concentrations. The signal was detected using HP-labeled anti-E tag antibody and HRP-labeled anti-mouse antibody f or ScFv and Mab, respectively. Results represent 30 minute readings after the addition of substrate.

FIG. 14 represents the results of ELISA based on the calculations discussed above. The ELISA data showed that MA116-15 ScFv was at least as reactive as the 1A4A-1 Mab in recognizing VEE antigen. Indeed, at higher protein concentrations, MA116-15 ScFv appeared to be more reactive than the 1A4A-1 Mab. , Mab 1A4A1 reached its maximum reactivity at approximately 315 ng protein; with further additions of Mab protein, reactivity with the VEE antigen appeared to be inhibited.

Discussion

In this invention, the inventors report successful utilization of a molecular engineering approach to enhance the functional reactivity of a partially active ScFv antibody. The reactivity of VEE ScFv A116 was enhanced at least four-fold in recognition of VEE whole virus antigen. The engineering strategy employed PCR-based site directed mutagenesis to re-introduce three single bases, identified previously as deletions in the 5 prime end of the $V_L$ gene of A116 clone. Introduction of these bases was predicted to repair a localized frame-shift in the N-terminal framework-1 region of the light chain of A116 ScFv antibody. Five clones (MA116-4, MA116-6, MA116-14, MA116-15, and MA116-16) were identified with potential enhanced reactivity to VEE whole virus antigen. These five MA116 clones were analyzed in detail to elucidate the molecular changes responsible for enhanced reactivity with target VEE antigen.

The strategy employed PCR-based site directed mutagenesis to re-introduce the three deleted bases. Two primers were synthesised for this purpose in the region of repair, located adjacent to each other but in opposite directions i.e., one forward and one reverse. The primers carried the bases to be inserted in the designated regions. The whole plasmid carrying A116 ScFv was PCR-amplified using the synthesized primers with the three insertions, thereby incorporating the three bases in the sequence of A116 gene. The introduction of the three bases and the repair of the framework-1 region was determined by DNA sequencing of the re-engineered A116 clones.

The PCR-based site directed mutagenesis of A116 ScFv gene was successfully accomplished as evidenced by the fact that only two out of the 16 MA116 clones analyzed, showed XhoI digestion patterns which were identical to the un-mutagenized parental A116 clone. The remaining 14 MA116 clones showed incorporation of at least one base insertion as indicated by the loss of XhoI site in the 5 prime end of the VL geneThis corresponds to a mutagenesis rate of ~90%.

Figure 9:
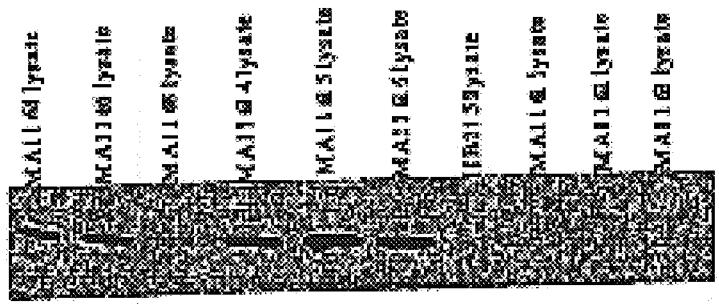

Since the mutagenesis strategy included PCR amplifications, the chance the unintended changes might occur, leading to nonsense mutations in the ORF was high. For this reason, it was important to screen the MA116 re-engineered clones by Western blot, to select those clones that were expressing the ScFv. Out of the 14 mutagenized MA116 clones, as demonstrated by XhoI digestion, only five actually expressed a full length 30 KDa ScFv product (FIG. 9). Our interpretation of these results is that there was introduction of unintented nucleotide changes, leading to nonsense mutations, as opposed to non-insertion of intended mutations. Since base insertions were incorporated into the primers which become part of every PCR amplified DNA molecule, it would be a rare event where the insertions would be deleted. A more common occurrence would be the introduction of unintented changes due to low fidelity of the proof reading ability of thermal polymerases. Some of these unintended changes would lead to nonsense or frameshift mutations, resulting in lack of expression of protein product. This interpretation of events is strengthened by observations made from clones MA116-2 and MA116-6. Although both of these clones exhibited XhoI digestion patterns identical to the non-mutagenized A116, MA116-2 did not express ScFv protein, probably due to introduction of nonsense mutations in the ORF. On the other hand, MA116-6 showed expression of normal ScFv protein.

ELISA results (FIG. 10) indicated that the MA116 clones showed variability in reactivity with the VEE antigen. Based on the reactivity with VEE antigen by ELISA, MA116 clones could be placed into three groups relative to the ELISA reactivity demonstrated by the parental A116 clone. MA116-15 was in Group A (functionally the most reactive group), with at least four-fold higher reactivity with VEE antigen than the parental A116 clone. MA116-14 and MA116-16 were in Group B, with moderately higher reactivity (~2.5 times higher than A116). MA116-4 and MA116-6 were in Group C (the least reactive group), with reactivity less than A116. Since equal amounts of total cellular proteins were added in ELISA for each of these clones, it is likely that the variable reactivities of Groups A, B, and C, as defined above, resulted from molecular differences at the gene level. However, to prove this assumption, sequencing of the complete ScFv gene for each of these clones was essential.

Complete nucleotide sequencing of the five MA116 clones was undertaken to determine the nature of the changes that had occurred at the gene level and to relate these changes to the observed functional reactivity of the ScFv produced. The sequencing data presented in FIG. 11 clearly demonstrates that there were significant molecular changes at the gene level that could, theoretically, be responsible for differences in reactivity at the protein level.

To explore the structure to function relationship in MA116 clones, FIG. 12 was generated from the information reduced from the complete nucleotide sequences of A116-16 and the five MA116 clones. The first 13 amino acids from the light chain of each of the clones belonging to reactive Groups A, B, and C were compared to the consensus amino acid sequence of the framework-1 region. The consensus sequence was developed by Kabat and Wu [15] after analyzing more than 200 light chain antibody sequences. From analysis of the data in FIG. 12, it can be proposed that the level of reactivity of the re-engineered ScFv proteins would be directly proportional to the percent identity with the consensus mouse amino acid sequence, with the exception of MA116-16. Thus, it can be observed that the amino acid sequence of MA116-15 (reactive Group A) (the most reactive in function) was 90% identical to the consensus amino acid sequence. On the other hand, the amino acid sequence of the parental ScFv A116, which was minimally active, was only 40% identical with the consensus sequence. MA116-6 and MA116-4 were also significantly altered and framework-1, and showed minimal activity in ELISA. MA116-14 demonstrated moderate functional activity, as only 4 amino acids were altered. Although MA116-16 had only a point mutation, this mutation was located in Framework-1 of the heavy chain, and disrupted the structure in this region by replacement of the P with a S at residue 16, reducing the binding activity to a moderate level (FIG. 10, 12).

Since MA116-15 ScFv was found to be the most reactive clone, the MA116-15 ScFv product was purified. The purified protein was used to confirm the earlier results from whole cell lysates and to do a functional comparison with the parental 1A4A-1 MAb. The purification of MA116-15 ScFv protein, with minimal contaminating proteins, was clearly demonstrated (FIGS. 13A and 13B). Calculations of the total MA116-15 ScFv protein purified suggested a concentration of between 50–80 $\mu$g, with the highest concentration being in fraction six at roughly 6–10 ng/$\mu$L. This concentration is consistent with the results obtained by Coomassie staining and western blot (FIG. 13A). The sensitivity limit of Coomassie staining is ~100 ng of protein. Since 10 $\mu$L were loaded on the gel and the band was faintly visible, the concentration would fall within the range of 6–10 ng/$\mu$L. That purified MA116-15 ScFv protein was functional in recognizing VEE whole virus antigen, was clearly demonstrated (FIG. 13C). The ELISA interaction was highly specific to the presence of VEE whole virus antigen, as demonstrated by an 8–10-fold difference between VEE antigen-specific interaction and non-specific background interaction.

The most important result of this study was that the MA116-15 ScFv protein was shown by ELISA to be functionally as reactive with VEE antigen as the parent 1A4A-1 Mab, when functionally equimolar quantities of the two proteins were used (FIG. 14). Further experiments are needed to answer certain ambiguities of this result. One ambiguity, for example, is that at concentrations lower than 375 ng, 1A4A-1 MAb appeared to be as reactive as the MA116-15 ScFv, but at higher concentrations, the reactivity of 1A4A-1 Mab seemed to be inhibited. A number of explanations for this observation are plausable. It is possible that the antigen concentration was limiting for the 1A4A-1 MAb i.e. once the antigen was depleted and antibody was in excess, no further antigen-antibody interaction could occur with increasing additions of antibody. A second possibility is that ScFv molecules, being five times smaller than MAb molecules, had better accessibility to plate-bound antigen than did larger MAb molecules that were physically hindered. Future experiments are planned to examine and resolve this observed ambiguity.

Conclusions

A116 ScFv has been successfully re-engineered for enhanced reactivity with VEE whole virus antigen. MA116-15, an extremely reactive clone has been isolated. In the process of defining molecular changes responsible for the enhanced reactivity of this MA116-15 ScFv and other MA116 clones, amino acids key to ScFv functionality have been identified. These amino acids may play a significant role in the conformational and functional stability of the framework-1 region of the antibody light chain, which in turn may affect the overall function of the antibody molecule. MA116-15 ScFv protein has been purified and found to be highly reactive to VEE whole virus antigen. Initial results suggest that MA116-15 ScFv antibody is as reactive in recognizing VEE antigen as is the parent 1A4A-1 MAb.

The importance of this reactive MA116-15 ScFv clone is emphasized by the fact that the parent 1A4A-1 Mab is neutralizing for a number of different pathogenic VEE isolates. Future experiments planned include detailed characterization of this MA 116-15 ScFv and determination of the neutralizing capability of this re-engineered ScFv. This invention is also important in that it opens the door for future molecular modelling studies on different MA116 clones. Such studies would define the role played by some of the key amino acid residues in antibody stability and function. This MA116-15 ScFv can also be a good candidate for animal protection studies to evaluate the usefulness of ScFv antibodies as anti-viral therapeutic agents in vivo.

It is to be understood that the embodiments and variations shown and described herein are merely illustrative of the principles of this invention and that various modifications may be implemented by those skilled in the art without departing from the scope and spirit of the invention.

We claim:

1. A recombinant ScFv antibody against Venezuelan equine encephalitis (VEE) encoded by a polynucleotide comprising the nucleotide sequence shown in SEQ ID NO: 1.

2. A recombinant ScFv antibody against VEE comprising the amino acid sequence shown in SEQ ID NO: 2.

3. A recombinant ScFv antibody expressed from cloned gene sequences of Mab 1A4A1 hybridoma cells.

4. The recombinant ScFv antibody of claim 3, wherein said antibody has a mutated region located at framework-1 of said antibody, and said mutated region is caused by three individual nucleotide deletions in the cloned gene sequences.

5. The recombinant ScFv antibody of claim 4, wherein said mutated region is in the N-terminal region of the $V_L$.

6. A recombinant ScFv antibody against Venezuelan equine encephalitis (VEE) encoded by a polynucleotide comprising the nucleotide sequence shown in SEQ ID NO: 3.

7. A recombinant ScFv antibody against VEE encoded by a polynucleotide comprising the nucleotide sequence shown in SEQ ID NO: 4.

8. A recombinant ScFv antibody against VEE encoded by a polynucleotide comprising the nucleotide sequence shown in SEQ ID NO: 5.

9. A recombinant ScFv antibody against VEE encoded by a polynucleotide comprising the nucleotide sequence shown in SEQ ID NO: 6.

10. A recombinant ScFv antibody against VEE encoded by a polynucleotide comprising the nucleotide sequence shown in SEQ ID NO: 7.

11. The recombinant ScFv antibody of claim 10, wherein said antibody comprises an amino acid sequence which is 90% identical to the consensus amino acid sequence in mouse variable light chain framework-1 region.

12. The recombinant ScFv antibody of claim 10, wherein said antibody has a high degree of functional reactivity at its variable light chain framework-1 region.

13. The recombinant ScFv antibody of claim 12, wherein said framework-1 region comprises an amino acid sequence of DIELTQSPNSL.

14. A recombinant ScFv antibody, wherein said antibody is functionally as reactive with VEE antigen as its parental 1A4A-1 monoclonal antibody provided that functionally equimolar quantities of the two antibodies were used.

15. A method for detecting and identifying VEE comprising mixing the recombinant ScFv antibody of claim 14 with a sample, and detecting the binding of said antibody to said sample to detec and identify VEE.

16. The recombinant ScFv antibody of claim 1, wherein said antibody is strain A116-16.

17. The recombinant ScFv antibody of claim 6, wherein said antibody is strain MA116-6 and has an accession number of 191103-03.

18. The recombinant ScFv antibody of claim 7, wherein said antibody is strain MA116-4 and has an accession number of 191103-02.

19. The recombinant ScFv antibody of claim 8, wherein said antibody is strain MA116-14 and has an accession number of 191103-04.

20. The recombinant ScFv antibody of claim 9, wherein said antibody is strain MA116-16 and has an accession number 191103-06.

21. The recombinant ScFv antibody of claim 10, wherein said antibody is strain MA116-15 and has an accession number 191103-05.

22. The recombinant ScFv antibody of claim 3, wherein said cloned gene sequences comprise the nucleotide sequence shown in SEQ ID NO: 1, 3, 4, 5, 6 or 7.

23. The recombinant ScFv antibody of claim 4, wherein said cloned gene sequences comprise the nucleotide sequence shown in SEQ ID NO: 1, 3, 4, 5, 6 or 7.

24. The recombinant ScFv antibody of claim 5, wherein said cloned gene sequences comprise the nucleotide sequence shown in SEQ ID NO: 1, 3, 4, 5, 6 or 7.

25. The recombinant ScFv antibody of claim 14, wherein said antibody is encoded by a polynucleotide comprising the nucleotide sequence shown in SEQ ID NO: 7.

26. The method for detecting and identifying VEE of claim 15, wherein said antibody is encoded by a polynucleotide comprising the nucleotide sequence shown in SEQ ID NO:7.

27. A polynucleotide comprising the nucleotide sequence shown in SEQ ID NO: 1, 3, 4, 5, 6 or 7.

* * * * *